United States Patent
Kim et al.

(10) Patent No.: US 7,485,619 B2
(45) Date of Patent: Feb. 3, 2009

(54) ANTIMICROBIAL AGENT

(75) Inventors: Yeon Sook Kim, Department of Oral Pathology, College of Dentistry, Kangnung National University, Chibyon-dong, Gangneung, Gangwon-do (KR); Suk Keun Lee, Department of Oral Pathology, College of Dentistry, Kangnung National University, Chibyon-dong, Gangneung, Gangwon-do (KR); Soo Il Chung, 6839 Old Stage Rd., Rockville, MD (US) 20852-4359; Sang Chul Park, Gyeong-Gi Do (KR)

(73) Assignees: Yeon Sook Kim, Gangwon-do (KR); Suk Keun Lee, Gangwon-do (KR); Soo Il Chung, Rockville, MD (US)

( * ) Notice: Subject to any disclaimer, the term of this patent is extended or adjusted under 35 U.S.C. 154(b) by 74 days.

(21) Appl. No.: 11/307,316

(22) Filed: Jan. 31, 2006

(65) Prior Publication Data

US 2006/0172940 A1    Aug. 3, 2006

Related U.S. Application Data

(60) Provisional application No. 60/648,815, filed on Jan. 31, 2005.

(51) Int. Cl.
*C07K 14/00* (2006.01)
(52) U.S. Cl. .......................................... 514/2; 530/300
(58) Field of Classification Search ................. 530/300; 514/2
See application file for complete search history.

(56) References Cited

U.S. PATENT DOCUMENTS

| | | | |
|---|---|---|---|
| 4,136,173 A | 1/1979 | Pramoda et al. |
| 4,136,177 A | 1/1979 | Lin et al. |
| 4,136,178 A | 1/1979 | Lin et al. |
| 4,758,595 A | 7/1988 | Ogunbiyi et al. |
| 4,861,760 A | 8/1989 | Mazuel et al. |
| 5,212,162 A | 5/1993 | Missel et al. |
| 5,221,732 A | 6/1993 | Chen et al. |
| 5,264,207 A | 11/1993 | Bommelaer et al. |
| 5,912,231 A | 6/1999 | Houghten et al. |
| 6,143,498 A | 11/2000 | Olsen et al. |
| 6,316,594 B1 | 11/2001 | Kim et al. |
| 6,545,140 B1 | 4/2003 | Harmon et al. |
| 6,872,705 B2 | 3/2005 | Lyons |
| 6,916,782 B1 | 7/2005 | Lamberty et al. |

FOREIGN PATENT DOCUMENTS

| | | |
|---|---|---|
| WO | WO 94/13333 A1 | 6/1994 |
| WO | WO 96/13164 A1 | 5/1996 |
| WO | WO 00/24378 A1 | 5/2000 |

OTHER PUBLICATIONS

Andreu et al. 1998; Animal antimicrobial peptides: An overview. Biopolymers (Peptide Science) 47: 415-433.*
Smet et al. 2005. Human antimicrobial peptides: defensins, cathelicidins and histatins. Biotechnology Letters 27: 1337-1347.*
Kim et al., EMBL No. AY177672, Sequence published Jun. 1, 2003.

* cited by examiner

*Primary Examiner*—Karen Cochrane Carlson
(74) *Attorney, Agent, or Firm*—Joseph Hyosuk Kim; JHK Law

(57) ABSTRACT

The present application discloses a therapeutic antimicrobial composition comprising mucocidin antimicrobial peptides or analogue or fragments thereof having antimicrobial activity.

22 Claims, 4 Drawing Sheets

Fig. 1

A. Nucleotide and predicted amino acid sequence of Mucocidin (Salvic, Genbank AY177672)

```
  1 gttttattta gcgt 15 atg cac gac ttc tgg gta ctg tgg gtt ctt ttg gaa tat ata tat aat tcc gcg tgt agt
     M   H   D   F   W   V   L   W   V   L   L   E   Y   I   Y   N   S   A   C   S
 75 gta ctg tca gct acg tca agt gtg agc agc cgg gtg tta aac aga agt ctc cag gtg aag
     V   L   S   A   T   S   S   V   S   S   R   V   L   N   R   S   L   Q   V   K
135 gtg gtt aaa atc acc aac tga ttctcacc aggagacaat catttgt
     V   V   K   I   T   N   *   (SEQ ID NO:2)
181 tgtattacac gttttcttaa attctatgtt caaattttct aattagttat tatccaaagg
241 ttacttttgg tgaatgtgag gaatcaactg acacaaatag acaaagtcgt aaaataaaaa
301 cctaaatctg cactttgaat gttttggaca aaatattcta aaatctaaaa gttgatcagt
361 gcaagagaaa cgatgtaatg tctgtgatgt ctcaccttca gattgtggct tcagtaccgt
421 gattatgcaa tattagttat gtatgtatgt atattagtta ttatgtaata ttagtgtgat
481 gagcaaaaga aaagaatta aaaaataaaa tgggtgaaaa aaaaaaa   (SEQ ID NO:1)
```

\*: translation terminal sequence, underlined: polyadenylated sequence

B. Northern blot

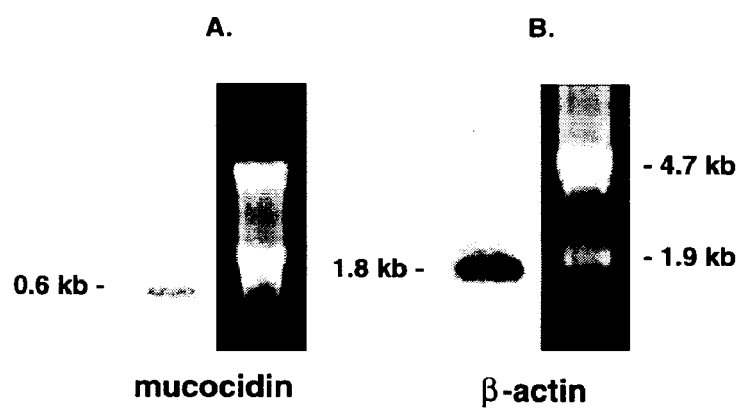

C. PCR

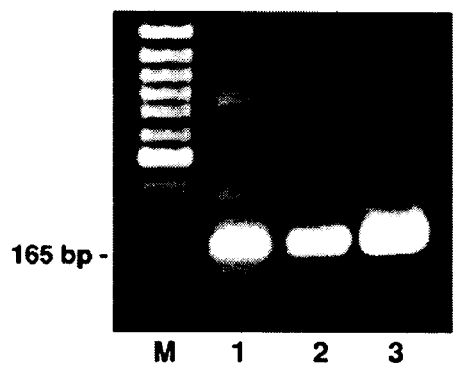

Fig. 2
A. Mucocidin induction by IPTG
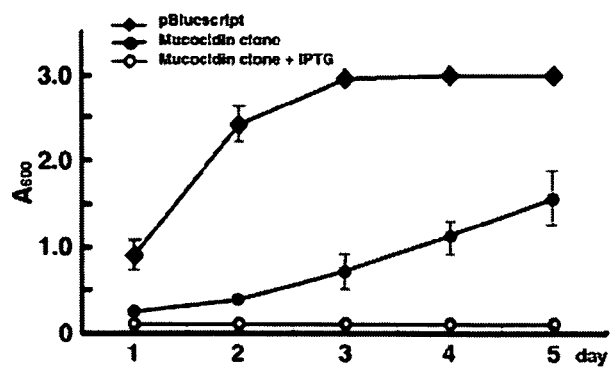
B. Colony killing assay
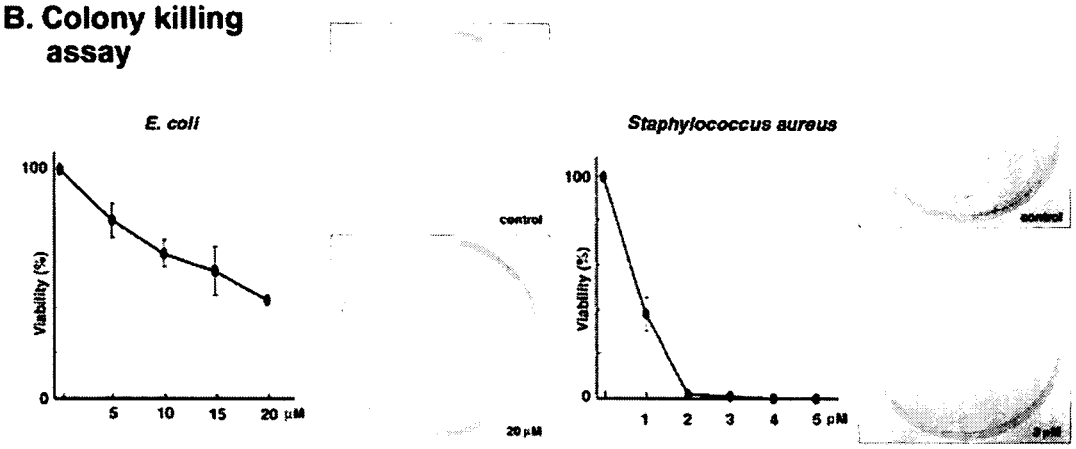
C. SEM observation
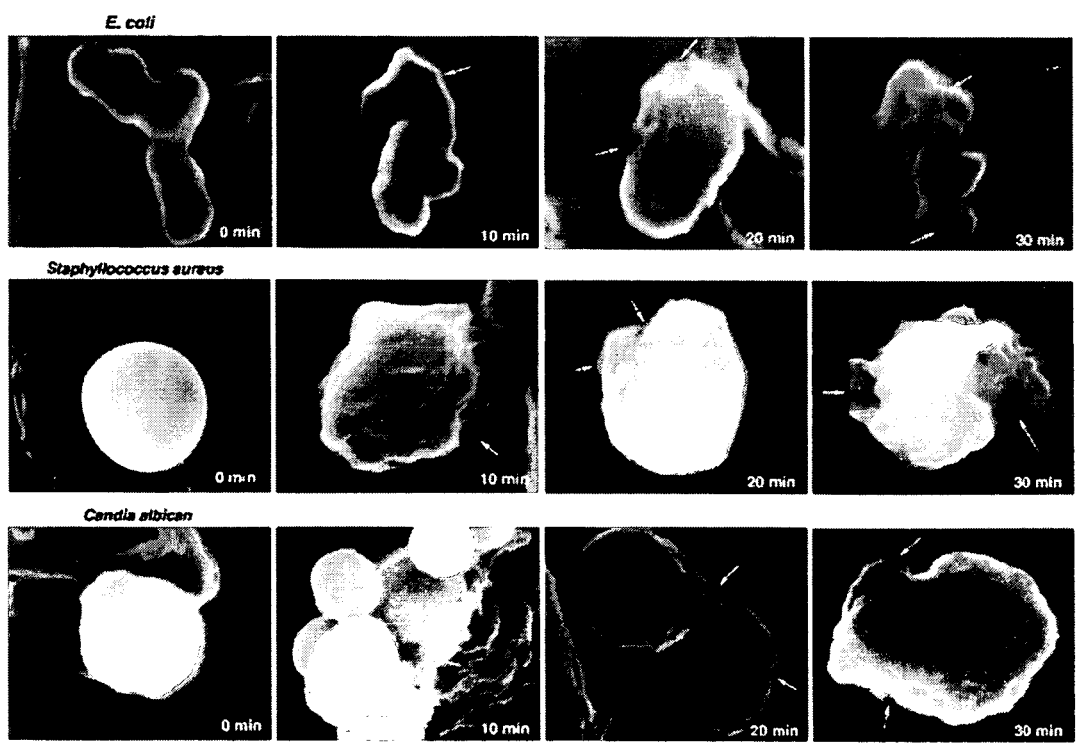

Fig. 3
A. mRNA array
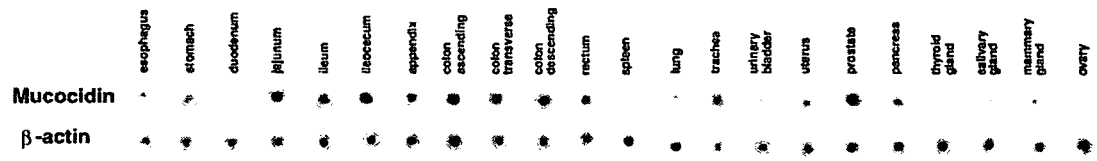
B. *in situ* hybridization
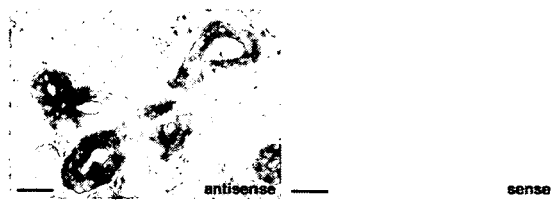
C. Immunohistochemistry
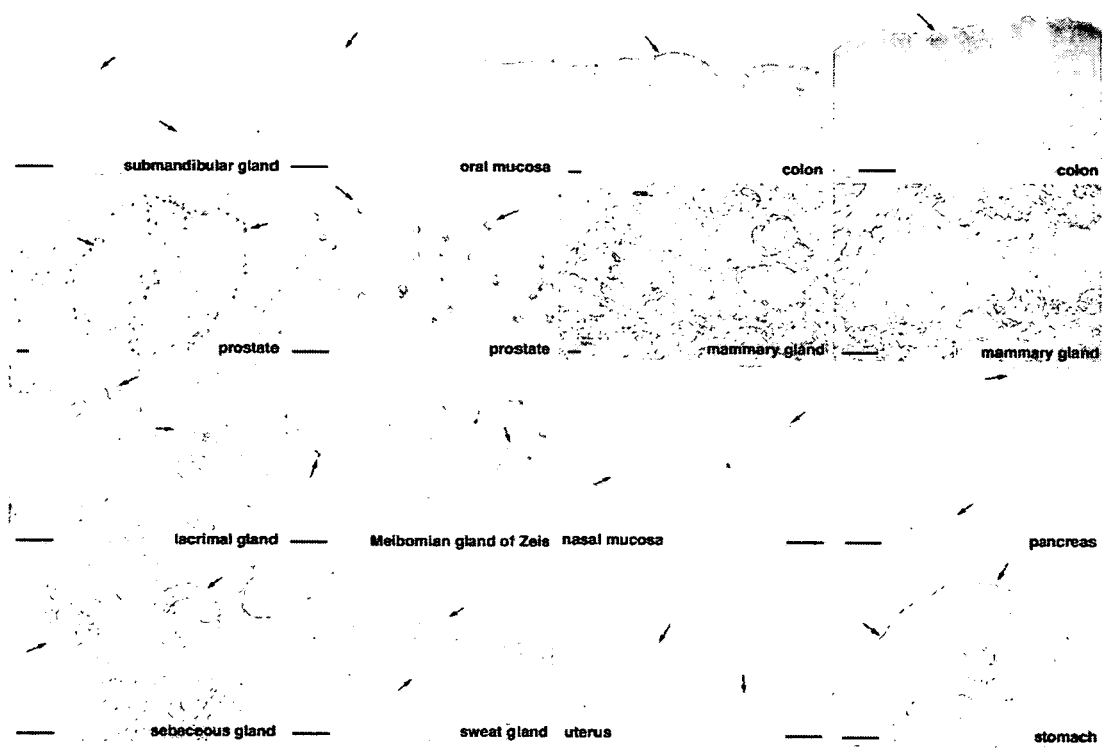

Fig. 4
A. Immunostain on oral exfoliated cell
a
b
c
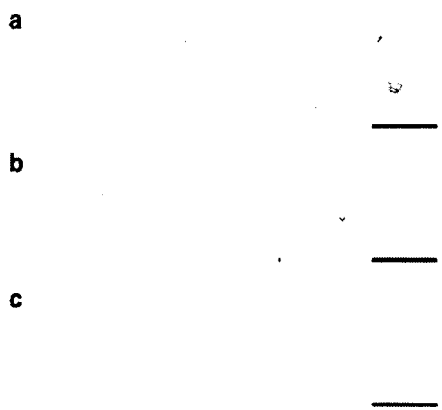
B. Western blot of Mucocidin
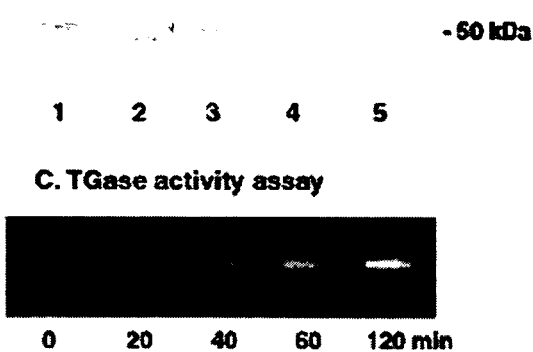
− 60 kDa
1   2   3   4   5
C. TGase activity assay
0   20   40   60   120 min
D. Isoelectric focus of Mucocidin
6.0 − 

ANTIMICROBIAL AGENT

CROSS-REFERENCE To RELATED APPLICATIONS

This application claims the benefit of U.S. Provisional Application No. 60/648,815, filed Jan. 31, 2005, which disclosure is herein incorporated by reference.

BACKGROUND OF THE INVENTION

1. Field of the Invention

The present application relates to the field of antimicrobial agents. The present application also relates to methods of inhibiting microbial growth using human derived peptides.

2. General Background and State of the Art

The mucosal tracts including oral and nasal cavity are exposed to a large spectrum of pathogenic and commensal microorganisms[1]. The mucosal integrity is preserved by various defense processes including physical barrier, luminal secretions such as mucins, antibacterial substances, the mucosal immune system, and the ability of the mucosa for rapid healing[1-6]. The homeostasis and integrity of the gastrointestinal mucosa ultimately depend upon a balance between defensive and aggressive factors. The mucosal barrier function was known to play a major role in mucosal protection against luminal bacteria, but the discovery of Toll-like receptors and antimicrobial peptides in the intestinal epithelium has opened a new concept of intestinal defense[7-9]. The oral cavity is known to teem with complex ever changing spectrum of large microbial populations and sustains repeated abrasions, yet maintains healthy mucosal integrity. Salivary secretions not only have essential functions in the digestive process but also play a critical role in protecting epithelium and mucosa from infection by batteries of secreted proteins, i.e. salivary mucins, proline-rich proteins, IgA, cystatins, elafin, protease, lysozyme, lactoferrin, lactoperoxidase, histatins, and also contains antimicrobial peptides such as defensins, and cathelicidin[8,10-12]. Antimicrobial peptides are the gene-encoded effector molecules of the innate immune system from insects to humans[13,14]. The peptides are active against a broad spectrum of Gram-positive and Gram-negative bacteria as well as some fungi and enveloped viruses[3,15,16]. These peptides play a major role in the management of the normal microflora. In mammals, the antimicrobial peptides are great contributors to antimicrobial efficacy of phagocytes such as neutrophils and macrophages, but the peptides are also expressed in epithelial cells[17]. In humans, there are three known families of antimicrobial peptides called defensins, cathelicidin and dermicidin. Defensins are divided into the α-defensins found in neutrophils, macrophages, and Paneth cells in the small intestine, and the β-defensins, which are found widespread in epithelial cells[18,19]. Cathelicidin is found mainly in neutrophils[16,20,21]. Members of this protein family share a highly conserved N terminus of 12 kDa named cathelin. Dermicidin is primarily found in the sweat gland although it was also expressed in skin and nerves[22].

During the investigation of orphan genes yet to be defined for their role in the human salivary gland, a clone was isolated from the subtracted cDNA library of human submandibular gland that was found to be non-redundant in the GenBank database (National Center for Biotechnology Information, NCBI), European Molecular Biology Laboratory (EMBL), and DNA DataBank of Japan (DDBJ), which also showed a characteristic positive expression in the salivary epithelium by RNA in situ hybridization. The C77-91 orphan gene was intensely expressed in the interlobular ductal and some serous acinar cells of human submandibular gland and was named "mucocidin" that expresses 46 amino acids peptide (pI=9.45) possessing an antimicrobial activity on *E. coli, Staphylococcus aureus, Pseudonomas aeruginosa, Aspergellous niger,* and *Candida albicans*. The gene encoding mucocidin is the same as the salvic gene registered in Genbank (AY177672)[23]. Mucocidin consists of a typical hydrophobic amino acid rich domain in the N-terminus and multiple consensus sequences of phosphorylation site and a single glutamine residue that may serve as a possible crosslinking site catalyzed by transglutaminase and four basic amino acids in the C-terminus. Northern blot analysis, in situ hybridization, gene microarray dot blot analysis and immunohistochemical staining of human organs and tissues using the antibody against the synthetic mucocidin peptide showed that it is widely expressed in various tissues and organs and more so in gastrointestinal tract and exocrine glandular ductal epithelium.

SUMMARY OF THE INVENTION

The present invention is directed to a therapeutic antimicrobial composition comprising mucocidin antimicrobial peptides or analogue or fragments thereof having antimicrobial activity. The fragment or variant of mucodicin may include residue number from about 12 to about 46, about 20 to about 46, about 22 to about 46, about 24 to about 46, or about 26 to about 46. The mucocidin, variant or fragment thereof may have at least four basic amino acids.

The invention also is directed to an isolated polynucleotide encoding a fragment or variant of mucocidin having antimicrobial activity. The invention also includes a vector comprising the polynucleotide and a host cell comprising the vector.

The invention is also directed to a method of producing a fragment or variant of mucocidin, comprising culturing the host cell under conditions such that a polypeptide is expressed, and recovering the polypeptide. Futher, the mucocidin, variant, or fragment thereof may comprise at least four basic residues.

In another aspect, the invention is directed to a method of inhibiting microbial growth comprising contacting a subject with the mucocidin, variant or fragment described above. The mucocidin, variant, or fragment thereof may comprise at least four basic residues. The microorganism may be bacteria, virus or fungus.

In still another aspect, the invention is directed to an ophthalmic composition comprising a carrier component, and a preservative component selected from the group consisting of mucocidin antimicrobial peptides or fragments thereof and mixtures thereof present in an amount effective as a preservative in said composition, wherein said composition is an oil-containing emulsion or an oil-containing suspension. The preservative component may be present in an effective amount less than about 10 milligrams per milliliter. The composition may further comprise an effective amount of a tonicity component to provide the composition with a desired osmolality. Further, the preservative component may be a mucocidin antimicrobial peptide.

In yet another aspect, the invention is directed to a method of producing mucocidin, variant or fragment thereof in a cell in a mammal comprising inserting a nucleotide sequence encoding the mucocidin, variant or fragment thereof in an expression vector, inserting the vector into a mammal and allowing the nucleotide sequence to be expressed.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 1A-1C show characterization of mucocidin mRNA. (A) Nucleotide and encoded amino acid sequence of mucocidin (Genbank AY177672)[23]. cDNA sequence and the amino acid sequence are as follows:

```
                                                           (SEQ ID NO:1)
gttttattta gcgtatgcac gacttctggg tactgtgggt tcttttggaa tatatatata   60
attccgcgtg tagtgtactg tcagctacgt caagtgtgag cagccgggtg ttaaacagaa  120
gtctccaggt gaaggtggtt aaaatcacca actgattctc accaggagac aatcatttgt  180
tgtattacac gttttcttaa attctatgtt caaattttct aattagttat tatccaaagg  240
ttacttttgg tgaatgtgag gaatcaactg acacaaatag acaaagtcgt aaaataaaaa  300
cctaaatctg cactttgaat gttttggaca aaatattcta aaatctaaaa gttgatcagt  360
gcaagagaaa cgatgtaatg tctgtgatgt ctcaccttca gattgtggct tcagtaccgt  420
gattatgcaa tattagttat gtatgtatgt atattagtta ttatgtaata ttagtgtgat  480
gagcaaaaga aaaagaatta aaaaataaaa tgggtgaaaa aaaaaaa              527

(SEQ ID NO:2)
MHDFWVLWVL LEYIYNSACS VLSATSSVSS RVLNRSLQVK VVITN                 46
```

(B) Northern blot analysis of mucocidin: Total RNA prepared from normal human submandibular gland section taken from a surgical excision of patient's tissues was used. Left gel shows the mucocidin mRNA hybridized with the mucocidin cDNA (C77-91 clone) labeled with biotinylated-dCTP and appeared as 0.53 kb with good level of expression. To normalize the amount of RNA present in the blots, β-actin probe (corresponding to nt 541-1201 of GenBank NM_001101) was also used as reference in the same method. (C) PCR was simultaneously performed using the primers specific for the open reading frame of mucocidin gene and template DNAs of human submandibular gland cDNA, human genomic DNA, and C77-91 plasmid DNA. lane 1, lane 2, lane 3.

FIGS. 2A-2C show antimicrobial activity of mucocidin. (A) The growth rate of $E.\ coli$ ($0.5\times10^3$) containing pBluescript SK plasmid with mucocidin cDNA insert and the control $E.\ coli$ containing plasmid alone in 20 ml LB broth cultured for 5 days. Cell growth was monitored by Absorbance at 600 nm ($A_{600}$). Induction of vector expression by 20 μL isopropyl-B-D-thiogalactopyranoside (IPTG 1 mM) is on the bottom line. Each point represents average of five experiments. (B) Bactericidal activity of synthetic mucocidin peptide was measured by the percent colony formation units of $E.\ coli$ and $Staphylococcus\ aureus$. Cells ($5\times10^5$) were cultured in 100 μL in IB broth containing 0, 5, 10, 20 μM concentration of mucocidin. After one hour, cell viability was determined by plating 300 μL aliquots of the 200 fold diluted cultured cell broth on LBA or TSA plates, respectively. Top plate shows the negative control with no mucocidin peptide and bottom plate contains mucocidin (20 μM for $E.\ coli$ and 3 μM for $S.$ $aureus$). Graph shows the average of five experiments as the percent viability of each microbe on each plate containing different concentrations of mucocidin peptide. (C) Scanning electron micrographs of $E.\ coli$, $Staphylococcus\ aureus$ and $Candida\ albicans$ incubated with 10, 20, 150 μM mucocidin, respectively for 10, 20 and 30 min, and they were immediately fixed with glutaraldehyde, dried on the Millipore membrane, and coated with gold. Note abnormal morphologies of each microbe where loss and shrinkage of original cell shapes as the time lapses. All photographs were taken at the same magnification. Scale bar, 1 μm.

FIGS. 3A-3C show tissue distribution of mucocidin by Gene Array, in situ hybridization and immunohistochemistry. (A) Mucocidin distribution was estimated by using tissue mRNA arrays by hybridizing with mucocidin cDNA. The mRNA array membrane containing the mRNA extracts from esophagus, stomach, duodenum, jejunum, ileum, ileocecum, appendix, ascending colon, transverse colon, descending colon, rectum, spleen, lung, trachea, bladder, uterus, prostate, pancreas, thyroid gland, salivary gland, mammary gland, and ovary (made available from BD Biosciences, Palo Alto, Calif.) were hybridized with the mucocidin cDNA labeled with biotinylated dCTP and visualized by chemiluminescent detection. (B) in situ hybridization with digoxigenin UTP labeled sense probe that was transcribed in vitro (negative control) or antisense probe for mucocidin showed that mucocidin was expressed heavily in the ductal cells of human submandibular gland. (C) Immunohistochemistry of mucocidin was assessed with rabbit mono-specific antibody and a secondary rabbit IgG antibody. As a specific control, tissue sections were incubated with secondary antibody. Immunostaining of submandibular gland, oral mucosa, colon, and prostate gland, lactating mammary gland, lacrimal gland, Meibomian gland of Zeis, nasal mucosa, pancreas, sebaceous gland, sweat gland, uterus, and stomach showed all positive reaction of mucocidin in the localized region of each tissue. Relative magnification of picture is indicated by bar length (50 μm). Arrows indicate the heavy expression sites of mucocidin in each organs and tissues.

FIGS. 4A-4B show immunostaining of cornified cell envelopes of exfoliated epithelial cells and Western-blot analysis of mucocidin from body fluids and tissue and MDC incorporation into mucocidin. (A) The cornified cell envelopes prepared from the exfoliated epithelial cells were immunostained with mucocidin antibody. Scale bar: 5 μm. (B)

Western blot analysis of tissue extract and body fluids: slot 1: synthetic mucocidins slot 2: submandibular gland extract, slot 3: parotid saliva, slot 4: mixed saliva, slot 5: seminal fluid. (C) Transglutaminase 2 catalyzed monodansylcadaverine (MDC) incorporation into mucocidin peptide separated by SDS PAGE and time dependent incorporation of MDC into mucocidin: slot 1: control sample without $Ca^{++}$ ion, slot 2: 20 min, slot 3: 40 min, slot 4: 1 h, and slot 5: 2 h. (D) Isoelectric focusing of isolated salivary mucocidin: Focused protein bands were detected by immuno-staining.

DETAILED DESCRIPTION OF THE PREFERRED EMBODIMENTS

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids added to or subtracted from the N-terminus or C-terminus may be included so long as the functional activity such as its antimicrobial activity is present.

As used herein, administration "in combination with" one or more further therapeutic agents includes simultaneous (concurrent) and consecutive administration in any order.

As used herein, "amino acid" and "amino acids" refer to all naturally occurring L-(x-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

In one aspect, the polypeptide variants of the present invention may contain any number of amino acids or alterations of amino acids, so long as the polypeptide variant includes a sequence that is at least about 70%, 75%, 80%, 85%, 90%, 95%, 96%, 97%, 98% or 99% identical to the polypeptide sequence represented by SEQ ID NO:2, and the presence of the variations do not hinder the anti-microbial activity of the polypeptide.

Applicants for the first time discovered that mucocidin and certain fragments thereof have anti-microbial properties, and thus it would be within the purview of a person of skill in the art to make certain variations to the sequence, which retains the anti-microbial activity.

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains (T. E. Creighton, Proteins: Structure and Molecular Properties, W. H. Freeman & Co., San Francisco, pp. 79-86 (1983)).

As used herein, "effective amount" is an amount sufficient to effect beneficial or desired clinical or biochemical results. An effective amount can be administered one or more times. For purposes of this invention, an effective amount of an anti-microbial compound is an amount that is sufficient to kill, reverse, slow or delay the progression of microbial proliferation.

As used herein, "fragment" refers to a part of a polypeptide, which retains usable and functional characteristics.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "sample" or "biological sample" is referred to in its broadest sense, and includes any biological sample obtained from an individual, body fluid, cell line, tissue culture. As indicated, biological samples include body fluids, such as semen, saliva, lymph, sera, plasma, urine, synovial fluid, spinal fluid and so on. Methods for obtaining tissue biopsies and body fluids from mammals are well known in the art. In addition, a "biological sample" obtained from a patient can be referred to either as a "biological sample" or a "patient sample." It will be appreciated that analysis of a "patient sample" need not necessarily require removal of cells or tissue from the patient.

As used herein, "subject" may refer to a mammal or a substrate such as a surface, which may be contaminated with microorganisms.

Mucocidin

In the present application, the isolation of novel human gene encoding an antimicrobial peptide with a broad spectrum of activity from salivary gland is described. This human gene designated as mucocidin showed no homology to known antimicrobial peptide. This peptide is specifically and constitutively expressed in mucosal epithelia and exocrine glandular ductal cells, secreted into mucosal fluid and glandular secretion, formed tight complex with cell surface molecule(s) and crosslinked to form stable protective cell surface barrier. Unlike other known antimicrobial peptides, the entire coding sequence (46 amino acids) peptide possessed antimicrobial activity without any prior proteolytic processing.

The presence of a peptide-mediated defense facilitates epithelial protection without involvement of inflammatory mediators. Until now, peptide-mediated antimicrobial defense was assumed to rely on a limited number of compounds such as the widespread appearance of naturally occurring antibacterial proteins and peptides including defensins and cathelicidins[1,3,5,6]. But abundance and distribution and in vitro/vivo activity has not been fully elucidated. Finding of the novel human antimicrobial peptide in the mucosal epithelium and new mechanism of protective barrier formation would strengthen the effectiveness of the innate immune system. Defensins, the major group of bactericidal peptides in humans, form two structurally distinct groups: α-defensins mainly found in neutrophiles and Paneth cells of the small intestine and β-defensins, mainly synthesized by epithelial cells[18,19]. LL-37, a 37 residue antimicrobial peptide is the only human cathelicidin located in neutrophiles, lymphocytes, and various epithelial cells[20,32]. However, heavy expression of mucocidin in the surfacing top segments of villi in the colon epithelium (FIG. 3C) allowed visualization of the formed fortified protective barrier in the heavily infested sites without interfering with the adjusted mix of commensal and pathogenic microbe populations.

Mucocidin crosslinking to epithelial cells is a novel mechanism of stable protective barrier formation. Evidence of such covalent attachment of salivary proteins to cell envelope proteins via TGase catalyzed reaction in the exfoliated epithelial cells of oral cavity has been demonstrated with other salivary proteins[33]. Such mucocidin crosslinking reaction will likely occur in all mucosal epithelium and also in skin (cornified cell envelope). However, such crosslinking reaction would depend upon the availability of a third component, TGase. Finding of strong immunostaining of stomach epithelia (FIG. 3D) whose acidic pH environment likely limits the TGase catalysis showed that secreted mucocidin could be bound to epithelium without being crosslinked.

Immunostaining of human prostate gland also showed possible storage of synthesized mucocidin in prostate cellular compartment where it is likely secreted upon ejaculatory signal and finding fair levels of mucocidin in the human seminal fluid suggests that it likely plays a role in protecting sperm cells in the seminal fluid. On the other hand, the secretory unit of submandibular gland consists mainly of acinar cells, ductal cells to support saliva secretion, and myoepithelial cells, which functions as contractile smooth muscle. Heavy expression of mucocidin in the ductal cells and light expression in acinar cells would likely support that mucocidin is constantly secreted with salivary fluid and regulated differently from the serous acinar cells stored salivary proteins. Also, heavy expression in the olfactory mucosa ciliated epithelia, tonsil, and oral mucosa again support mucocidin's role in mucosal protection.

As modeling study suggests, like many antimicrobial peptides including insect cecropins, frog magainins, and some mammalian cathelicidins, mucocidin likely adopts an amphipathic α-helix and is enriched in arginine or lysine residues. Therefore, mode of this peptide action in response to microorganism is probably similar to that of the cationic defensins[34], which can bind to anionic components of the target membrane and kill the microorganism by pore formation and permeabilization of the cell membrane as demonstrated by SEM study (FIG. 2C). Indeed, the deletion peptide study supports such mechanism where a deletion of one arginine residue decreases the activity by three fold.

The results show that mucocidin is secreted by mucosal epithelial cells of gastrointestinal, respiratory oral pharyngeal tract and exocrine glands into the mucosal fluid, and may be tightly associated with and crosslinked to epithelia to form a stable functional protective barrier. The coding sequence of the expressed cDNA or synthetic peptide was bactericidal against *E. coli*. The peptide is also active against *S. aureus*, and *C. albicans*. Mucocidin showed no homology to known antimicrobial peptides and was dominantly expressed in mucosal epithelial cells. This novel antimicrobial peptide may play a key role in the innate immune response of the mucosal tracts.

Mucocidin Polynucleotide and Polypeptide

The present invention provides isolated nucleic acid molecules comprising a polynucleotide encoding an antimicrobial peptide having the amino acid sequence shown in SEQ ID NO:2, which was determined by sequencing a cloned cDNA.

The present invention also provides the native form(s) of the antimicrobial peptide protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature antimicrobial peptide polypeptides having the amino acid sequence encoded by the cDNA of SEQ ID NO:1.

As indicated, nucleic acid molecules of the present invention may be in the form of RNA, such as mRNA, or in the form of DNA, including, for instance, cDNA and genomic DNA obtained by cloning or may be produced synthetically. The DNA may be double-stranded or single-stranded. Single-stranded DNA or RNA may be the coding strand, also known as the sense strand, or it may be the non-coding strand, also referred to as the anti-sense strand.

The present invention further relates to variants of the nucleic acid molecules of the present invention, which encode portions, analogs or derivatives of the antimicrobial peptide protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the antimicrobial peptide protein or portions thereof. Also especially preferred in this regard are conservative substitutions.

Further embodiments of the invention include isolated nucleic acid molecules comprising a polynucleotide having a nucleotide sequence at least 95%, 96%, 97%, 98% or 99% identical to a nucleotide sequence encoding the polypeptide having the amino acid sequence in SEQ ID NO:2.

By a polynucleotide having a nucleotide sequence at least, for example, 95% "identical" to a reference nucleotide sequence encoding an antimicrobial peptide is intended that the nucleotide sequence of the polynucleotide is identical to the reference sequence except that the polynucleotide sequence may include up to five point mutations per each 100 nucleotides of the reference nucleotide sequence encoding the antimicrobial peptide polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 can be determined conventionally using known computer programs such as the Bestfit program (Wisconsin Sequence Analysis Package, Version 8 for Unix, Genetics Computer Group, University Research Park, 575 Science Drive, Madison, Wis. 53711). Best fit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1, irrespective of whether they encode a polypeptide having antimicrobial peptide activity. This is because even where a particular nucleic acid molecule does not encode a polypeptide having antimicrobial peptide activity, one of skill in the art would still know how to use the nucleic acid molecule, for instance, as a hybridization probe or a polymerase chain reaction (PCR) primer. Uses of the nucleic acid molecules of the present invention that do not encode a polypeptide having antimicrobial peptide activity include, interalia, (1) isolating the antimicrobial peptide gene or allelic variants thereof in a cDNA library; (2) in situ hybridization (e.g., "FISH") to metaphase chromosomal spreads to provide precise chromosomal location of the antimicrobial peptide gene, as described in Verma et al., Human Chromosomes: A Manual of Basic Techniques, Pergamon Press, New York (1 988); and Northern Blot analysis for detecting antimicrobial peptide mRNA expression in specific tissues.

Preferred, however, are nucleic acid molecules having sequences at least 95%, 96%, 97%, 98% or 99% identical to a nucleic acid sequence shown in SEQ ID NO:1, which do, in fact, encode a polypeptide having antimicrobial peptide protein activity. By "a polypeptide having antimicrobial peptide activity" is intended polypeptides exhibiting antimicrobial peptide activity in a particular biological assay.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown in SEQ ID NO:1 will encode a polypeptide "having antimicrobial peptide protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having antimicrobial peptide protein activity. This is because the skilled artisan is fully aware of amino acid substitutions that are either less likely or not likely to significantly affect protein function (e.g., replacing one aliphatic amino acid with a second aliphatic amino acid).

Vectors and Host Cells

The present invention also relates to vectors which include the isolated DNA molecules of the present invention, host cells which are genetically engineered with the recombinant vectors, and the production of antimicrobial peptide polypeptides or fragments thereof by recombinant techniques. Also, constructed vectors can be utilized for gene therapy for chronically infection prone and genetically mucocidin deficient patient.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the $E. coli$ lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in $E. coli$ and other bacteria. Representative examples of appropriate hosts include, but are not limited to, bacterial cells, such as $E. coli, Streptomyces$ and $Salmonella typhimurium$ cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

In addition to the use of expression vectors, the present invention further includes novel expression vectors comprising operator and promoter elements operatively linked to nucleotide sequences encoding a protein of interest.

The antimicrobial peptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Human Antimicrobial Polypeptides and Fragments

The invention further provides an isolated antimicrobial peptide having the amino acid sequence encoded by the cDNA, or the amino acid sequence in SEQ ID NO:2, or a peptide or polypeptide comprising a portion of the above polypeptides.

It will be recognized in the art that some amino acid sequences of the antimicrobial peptide can be varied without significant effect of the structure or function of the protein. If such differences in sequence are contemplated, it should be remembered that there will be critical areas on the protein which determine activity.

Thus, the fragment, derivative or analog of the polypeptide of SEQ ID NO:2, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the antimicrobial peptide. The prevention of aggregation is highly desirable. Aggregation of proteins not only results in a loss of activity but can also be problematic when preparing pharmaceutical formulations, because they can be immunogenic. (Pinckard et al., Clin Exp. Immunol. 2:331 -340 (1967); Robbins et al., Diabetes 36:838-845 (1987); Cleland et al. Crit. Rev. Therapeutic Drug Carrier Systems 10:307-377 (1993)).

As indicated, changes are preferably of a minor nature, such as conservative amino acid substitutions that do not significantly affect the folding or activity of the protein. For instance, aromatic residues are Phenylalanine, Tryptophan, and Tyrosine. Hydrophobic residues are Leucine, Isoleucine, and Valine. Polar residues are Glutamine and Asparagine. Basic residues are Arginine, Lysine, and Histidine. Acidic residues are Aspartic Acid and Glutamic Acid. Small residues are Alanine, Serine, Threonine, Methionine, and Glycine.

Of course, the number of amino acid substitutions a skilled artisan would make depends on many factors, including those described above. Generally speaking, the number of amino acid substitutions for any given antimicrobial polypeptide will not be more than 46, 40, 45, 30, 25, 20, 15, 10, 5, 3, 2, or 1.

Amino acids in the antimicrobial peptide of the present invention that is essential for function can be identified by methods known in the art, such as site-directed mutagenesis or alanine-scanning mutagenesis known to those skills in the art.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell.

By a polypeptide having an amino acid sequence at least, for example, 95% "identical" to a reference amino acid sequence of a antimicrobial peptide is intended that the amino acid sequence of the polypeptide is identical to the reference sequence except that the polypeptide sequence may include up to five amino acid alterations per each 100 amino acids of the reference amino acid of the antimicrobial peptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxyl terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Therapeutics

The antimicrobial peptide of the present invention can be used as an antimicrobial agent for the treatment of fungal, bacterial or viral infections. The peptide of the present invention can be used for such treatment in a topical or systemic formulation for the treatment of acne, burns, eye infections, mouthwash, deodorant or topical fungicides. In addition, *C. albicans*, the common cause of mucocutaneous fungal disease in AIDS patients, which is extremely susceptible to several β-defensins, might be controlled in these individuals more effectively by a β-defensin-based therapeutic or in combination with existing drugs. The peptide of the present invention can be used also for treatment of chronic granulomatous gastrointestinal ulcer, chronic suppurative osteomyelitis, and chronic allergic dermatitis. Furthermore, the peptide can be utilized as preventative treatment for herpes simplex, and influena viral infections.

Modes of Administration

It will be appreciated that conditions caused by a decrease in the standard or normal level of antimicrobial peptide activity in an individual, can be treated by administration of the antimicrobial peptide. Thus, the invention further provides a method of treating an individual in need of an increased level of antimicrobial peptide activity comprising administering to such an individual a pharmaceutical composition comprising an effective amount of an isolated antimicrobial peptide of the invention, particularly a native form of the antimicrobial peptide, effective to increase the antimicrobial peptide activity level in such an individual.

As a general proposition, the total pharmaceutically effective amount of antimicrobial peptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the antimicrobial peptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed.

Pharmaceutical compositions containing the antimicrobial peptide of the invention may be administered orally, rectally, parenterally, intra-systemitcally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Therapeutic Composition

In one embodiment, the present invention relates to treatment for various diseases that are characterized by being treatable through application of antimicrobial agents.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (e.g., using slow release molecules by the intraperitoneal route or by using cells, e.g., monocytes or dendrite cells sensitized in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a peptide of the invention, care must be taken to use materials to which the peptide does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Topical Application to Wounds

According to the present invention, the mucocidin molecule in the form of liquid or powder can be applied directly onto a wound, i.e., sprinkled over the wound site. The mucocidin molecule applied to a sheet may be applied over the wound site, which is then dressed suitably to protect the wound and prevent the healing effects of the active ingredient from diminishing. Any commercially available or conventional wound dressing may be used in the present invention. The examples of commercially available wound dressings include, but are not limited to, COMPEEL®, DUODERM™, TAGADERM™ and OPSITE®.

The composition containing a pharmaceutically effective amount of the mucocidin peptide in combination with a pharmaceutically acceptable carrier can be formulated into a variety of forms by means known in the pharmaceutical art. The administration forms include, but are not limited to, conventional dosage forms of external preparation, e.g., liquid paints, sprays, lotions, creams, gels, pastes, liniments, ointments, aerosols, powders and transdermal absorbers. Actual methods for preparing administrable compositions will be known or apparent to those skilled in the art and are described in more detail in such publications as Remington's Pharmaceutical Science, 15$^{th}$ Edition, 1975, Mack Publishing Company, Easton, Pa. 18042 (Chapter 87: Blaug, Seymour), the contents of which are incorporated herein by reference.

In the external preparation of the present invention, suitable carriers can be chosen depending on the dosage forms and include, but are not limited to, hydrocarbons such as vaseline, liquid paraffin, and plasticized hydrocarbon gel (plastibase); animal and vegetable oils such as medium-chain fatty acid triglyceride, lard, hard fat, and cacao oil; higher fatty acid and alcohols and esters thereof such as stearic acid, cetanol, stearyl alcohol, and palmitic acid isopropyl; water-soluble bases such as Macrogol (polyethylene glycol), 1,3-butylene glycol, glycerol, gelatine, white sugar, and sugar alcohol; emulsifiers such as glycerine fatty acid ester, stearic acid polyoxyl, and polyoxyethylene/or curing castor oils; thickeners such as acrylic acid esters, and sodium alginates; propellants such as liquefied petroleum gas, and carbon dioxide; and preservatives such as paraoxybenzoic acid esters. The external preparation of the present invention can be prepared with the aforementioned carriers by methods well-known to those skilled in the art. In addition to said carriers, additives such as stabilizers, pigments, coloring agents, pH adjusting agents, diluents, surfactants, and antioxidants are, if necessary, used. The external preparation of the present invention can be applied to the tropical wound site by conventional methods.

The external preparation according to the present invention may be also used in adhesion onto a solid support such as a wound covering release layer. The adhesion is achieved by saturation of the solid support with a composition containing the mucocidin molecule. In one embodiment of the present invention, the solid support is first coated with an adhesion layer to improve the adhesion of the mucocidin molecule to the solid support. Exemplary adhesion materials include polyacrylate and cyanoacrylate. As such formulation, there is provided a number of commercially available products, including bandage having non-adhesive wound-covering release layer in a perforated plastic film by Smith & Nephew Ltd., BAND-AID® in thin strip, patch, spot and thermoplastic strip forms byjohnson & Johnson, CURITY® and CURAD® ("ouchless" type of bandage) by Kendall Co. (a division of Colgate-Palmolive Company), and STIK-TITE® (elastic strip) by American White Cross Labs, Inc.

In one embodiment, the pharmaceutical composition according to the present invention can be formulated into a liquid paint preparation by mixing the mucocidin molecule with physiologic saline at a fixed ratio by volume and adjusting the pH value of the resulting mixture to the range of from 3.5 to 6.5. In another embodiment, the pharmaceutical composition according to the present invention can be formulated into an ointment preparation by mixing the mucocidin molecule with a water-soluble ointment base and adding physiologic saline to the resulting mixture. Preferably, the pH value of the ointment is adjusted to the range of from 3.5 to 6.5.

According to the present invention, pharmaceutical carriers such as gels or microspheres may be used to promote the wound healing. A variety of microspheres of a polymer as carriers for one or more pharmaceutically or cosmetically active substances is described in U.S. Pat. No. 5,264,207, WO 2000/24378, WO96/13164 and WO 94/13333, the entire contents of which are incorporated herein by reference The pharmaceutical composition of the present invention can be used to treat a variety of wounds and infections in mammalian animals.

Generally, 2 to 5% by weight of the mucocidin molecule are administered per dose. The frequency of administration may range between twice daily and once per week. In a specific embodiment, full thickness defect wounds are treated with from 0.01 to 0.1 g/cm$^2$ of the pharmaceutical composition of the present invention daily, preferably from 0.02 to 0.09 g/cm$^2$, more preferably from 0.02 to 0.07 g/cm$^2$.

Ophthalmic Composition

The present invention also relates to preserved ophthalmic compositions, for example, useful in administering a therapeutic component to the eyes, and for example, to care for contact lenses, which include one or more peptides and/or peptide derivatives as antimicrobial agents.

Various compositions, such as solutions, emulsions and suspensions are used in association with administering therapeutic components to the eyes. For example, an oil-in-water emulsion may be used as a carrier for a therapeutic component to be administered to the eyes.

Use of single dose containers to store ophthalmic compositions prevents contamination and growth of microorganisms. However, single dose containers are inconvenient to use and are expensive for the consumer. Appropriate use of an effective preservative will allow for production of multidose containers of preserved ophthalmic compositions such as oil-in-water emulsions.

Various compositions are used in association with contact lenses to ensure that the lenses may be safely, comfortably and conveniently worn. Contact lens care compositions, for example, cleaning compositions, wetting compositions, conditioning compositions and the like, often utilize at least one preservative, depending on the type of composition, for preserving the lens care composition itself.

A preserved contact lens care composition has sufficient antimicrobial activity so that when the composition is contacted with a contact lens substantially no increase in the microorganism population on the lens or in the composition is obtained. A preserved contact lens care composition may be termed a microbiostatic composition. Contact lens care compositions are often preserved to prevent any substantial increase in, or to gradually decrease, the population of contaminating microorganisms in the compositions and, thereby, to extend their shelf life.

Various compounds are known for use as preserving agents in preserved ophthalmic compositions. Examples include thimerosal, benzalkonium chloride and chlorhexidine. However, these preserving agents are known to exhibit ocular toxicity which may result in irritation or sensitivity to the eye. Further, a soft contact lens, a rigid gas permeable contact lens (RGP) or a hard contact lens can absorb or adsorb these compounds. This causes the contact lens to retain the irritating compound and contributes to the eye irritation and eye sensitivity which may result.

The present compositions include effective preservatives to protect against growth of contaminating microorganisms. Importantly, such preserving activities are achieved using the present compositions with little or no risk of eye irritation or sensitivity.

In one embodiment of the invention, compositions useful for preserving ophthalmic compositions are provided. Such compositions include a mucocidin antimicrobial peptide, an analog of a mucocidin antimicrobial peptide or a mixture thereof present in an amount effective as a preservative. This effective amount may be less than about 10 milligrams per milliliter or less than about 1 milligram per milliliter or less than about 0.1 milligram per milliliter. Also included in the compositions is a therapeutic component. In a particularly useful embodiment of the invention, the compositions comprise mucocidin antimicrobial peptides. The compositions may also include water and an effective amount of a buffer to provide the compositions with a desired pH. Also, the compositions may include an effective amount of a tonicity component to provide the compositions with a desired osmolality.

The compositions exist in various forms. For example, the compositions may be an oil-in-water emulsion, a solution or a suspension. Also, provided is for a sole preservative to be used in accordance with the invention.

The compositions may be applied onto or into the eyes. For example, the compositions may be used as a surgical irrigant.

Exemplary mucocidin antimicrobial peptides include the peptides having the following amino acid sequences:

| | |
|---|---|
| M$^1$HDFWVLWVLLEYIYNSACSVLSATSSVSSRVLNRSLQVKVVKITN; | (SEQ ID NO:2) |
| E$^{12}$YIYNSACSVLSATSSVSSRVLNRSLQVKVVKITN$^{46}$; | (SEQ ID NO:3) |
| M$^1$HDFWVLWVLLEYIYNSACSVLS$^{23}$; | (SEQ ID NO:4) |
| A$^{24}$TSSVSSRVLNRSLQVKVVKITN$^{46}$; | (SEQ ID NO:5) |
| SSVSSRVLNRSLQVKVVKITN; | (SEQ ID NO:6) |
| VSSRVLNRSLQVKVVKITN; | (SEQ ID NO:7) |
| SRVLNRSLQVKVVKITN; | (SEQ ID NO:8) |
| VLNRSLQVKVVKITN; and | (SEQ ID NO:9) |
| SRVLNRSLQVKVVKIT. | (SEQ ID NO:10) |

Antimicrobial peptide mimetics are also contemplated for use with the present invention. Antimicrobial peptide mimetics may have a lower molecular weight than an average size antimicrobial peptide. These peptides may comprise components such as modified thiazole and/or oxazole moieties. Antimicrobial peptide mimetics may be membrane active molecules that function by disrupting cell membranes. At least one type of antimicrobial peptide mimetic can be obtained from Genaera Corp., Plymouth Meeting, Pa.

The antimicrobial agents must be compatible with the composition being preserved. The antimicrobial peptides should also be non-toxic to humans.

A second antimicrobial component can be employed in the present invention that is other than the first antimicrobial component. This second antimicrobial component can be selected from substantially non-oxidative antimicrobial components and mixtures thereof.

As used herein, substantially non-oxidative antimicrobial components include effectively non-oxidative organic chemicals, for example, synthetic polymers, which derive their antimicrobial activity through a chemical or physiochemical interaction with the microbes or microorganisms. Suitable non-oxidative antimicrobial components include, but are not limited to, quaternary ammonium salts used in ophthalmic applications such as poly[dimethylimino-2-butene-1,4-diyl]chloride, α-[4-tris(2-hydroxyethyl)ammonium]-dichloride (chemical registry number 75345-27-6, available under the trademark polyquarternium 1.® from ONYX Corporation), benzalkonium halides, and biguanides such as salts of alexidine, alexidine-free base, salts of chlorhexidine, hexamethylene biguanides and their polymers, antimicrobial polypeptides, and the like and mixtures thereof. A particularly useful substantially non-oxidative antimicrobial component is selected from polyhexamethylene biguanide (PHMB), N-alkyl-2-pyrrolidone, chlorhexidine, polyquaternium-1, hexetidine, bronopol, alexidine, ophthalmically acceptable salts thereof and mixtures thereof.

The salts of alexidine and chlorhexidine can be either organic or inorganic and are typically gluconates, nitrates, acetates, phosphates, sulphates, halides and the like. Generally, the hexamethylene biguanide polymers, also referred to as polyaminopropyl biguanide (PAPB), have molecular weights of up to about 100,000. Such compounds are known and are disclosed in Ogunbiyi et al U.S. Pat. No. 4,758,595, the disclosure of which is incorporated in its entirety herein by reference.

The substantially non-oxidative antimicrobial components useful in the present invention are preferably present in the liquid aqueous medium in concentrations in the range of about 0.000005% or about 0.00001 % to about 2% (w/v).

More preferably the substantially non-oxidative antimicrobial component is present in the liquid aqueous medium at an ophthalmically acceptable or safe concentration.

The concentration of preservative selected depends, for example, on the effectiveness of the specific preservative in preventing growth, or the killing, of bacteria, fungi, and/or protozoa in a preserved composition. Concentration of preservative selected may also depend on the effectiveness of the specific preservative in reducing the microbial load on a contact lens.

The present compositions in the form of aqueous suspensions may include excipients suitable for the manufacture of aqueous suspensions. Such excipients are suspending agents, for example, sodium carboxymethylcellulose, methylcellulose, hydroxypropyl-methylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, heptadeca-ethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof.

The present compositions in the form of oily suspensions may be formulated in a vegetable oil, for example, olive oil, castor oil, soy oil, sesame oil or coconut oil, or in a mineral oil such as liquid paraffin. Such suspensions may contain a thickening agent, for example beeswax, hard paraffin or cetyl alcohol.

The present compositions may also be in the form of oil-in-water emulsions. The oily phase may be a vegetable oil, for example, castor oil, olive oil, soy oil, or arachis oil, or a mineral oil, for example, liquid paraffin, and the like and mixtures thereof. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate.

Also included within the scope of this invention are preserved compounds which increase in viscosity upon administration to the eye. For example, "gelling polysaccharides" which are disclosed in U.S. Pat. No. 5,212,162 which is incorporated in its entirety herein by reference. Also disclosed in this patent are ophthalmic formulations containing carrageenans and furcellarans which are administered as partially gelled liquids which gel upon instillation into the eye. Additionally, U.S. Pat. Nos. 4,136,173, 4,136,177, and 4,136,1 78, disclose the use of therapeutic compositions containing xanthan gum and locust bean gum which are delivered in liquid form to the eye and which gel upon instillation. U.S. Pat. No. 4,861,760 discloses ophthalmological compositions containing gellan gum which are administered to the eye as non-gelled liquids and which gel upon instillation. Each of these four patents is incorporated in its entirety herein by reference.

Also within the scope of this invention are preserved oils, ointments, gels and the like.

The present compositions may include components, such as cyclodextrins, to enhance the solubility of one or more other components included in the compositions. Cyclodextrins are widely known in the literature to increase the solubility of poorly water-soluble pharmaceuticals or drugs and/or enhance pharmaceutical/drug stability and/or reduce unwanted side effects of pharmaceuticals/drugs. For example, steroids, which are hydrophobic, often exhibit an increase in water solubility of one order of magnitude or more in the presence of cyclodextrins. Any suitable cyclodextrin component may be employed in accordance with the present invention. The useful cyclodextrin components include, but are not limited to, those materials which are effective in increasing the apparent solubility, preferably water solubility, of poorly soluble active components and/or enhance the stability of the active components and/or reduce unwanted side effects of the active components. Examples of useful cyclodextrin components include, but are not limited to: β-cyclodextrin, derivatives of β-cyclodextrin, carboxymethyl-β-cyclodextrin, carboxymethyl-ethyl-β-cyclodextrin, diethyl-β-cyclodextrin, dimethyl-β-cyclodextrin, methyl-β- cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. As used herein, the term "derivatives" as it relates to a cyclodextrin means any substituted or otherwise modified compound which has the characteristic chemical structure of a cyclodextrin sufficiently to function as a cyclodextrin component, for example, to enhance the solubility and/or stability of active components and/or reduce unwanted side effects of the active components and/or to form inclusive complexes with active components, as described herein.

The specific cyclodextrin component selected should have properties acceptable for the desired application. The cyclodextrin component should have or exhibit reduced toxicity, particularly if the composition is to be exposed to sensitive body tissue, for example, eye tissue, etc. Very useful β-cyclodextrin components include β-cyclodextrin, derivatives of β-cyclodextrin and mixtures thereof. Particularly useful cyclodextrin components include sulfobutylether β-cyclodextrin, hydroxypropyl β-cyclodextrin and mixtures thereof. Sulfobutylether β-cyclodextrin is especially useful, for example, because of its substantially reduced toxicity.

The amount of cyclodextrin component in the present compositions should be effective to perform the desired function or functions in the present composition and/or perform the desired function or functions after administration to a human or animal. The amount of cyclodextrin component preferably is sufficient to complex at least in a major amount, and more preferably substantially all, of the active component in the present composition. In one useful embodiment, the amount of cyclodextrin component in the present composition is in the range of about 0.1% to about 30% (w/v) or more of the composition.

An additional component or additional components included in the present compositions may be selected from components which are conventionally used in one or more contact lens care compositions. For example, the present compositions may be formulated as preserving compositions, disinfecting compositions, cleaning compositions, wetting compositions, conditioning compositions, soaking compositions and the like. Examples of such additional components include buffering agents, cleaning agents, wetting agents, sequestering agents, viscosity builders, tonicity agents, nutrient agents, contact lens conditioning agents, antioxidants, pH adjustors, and the like. These additional components are each included in the present compositions in an amount effective to impart or provide the beneficial or desired property to the compositions. For example, such additional components may be included in the present compositions in amounts similar to the amounts of such components used in other ophthalmic compositions.

Also, the present compositions may be formulated to be useful in performing two or more contact lens care operations. For example, for contact lens care, a preserved disinfecting/cleaning composition, or a preserved cleaning/conditioning composition or even an all-purpose lens care composition may be formulated and such multi-functional compositions are included within the scope of the present invention.

A surfactant component may be included in the present compositions. The surfactant component preferably is nonionic. Exemplary surfactant components include, but are not limited to, nonionic surfactants, for example, polysorbates (such as Tween® 80), 4-(1,1,3,3-tetramethylbutyl) phenol/poly(oxyethylene) polymers (such as the polymer sold under the trademark Tyloxapol®), poly(oxyethylene)-poly(oxypropylene) block copolymers, glycolic esters of fatty acids and the like, and mixtures thereof. The surfactant may be selected from poly(oxyethylene)-poly(oxypropylene) block copolymers and mixtures thereof. Such surfactant components may be obtained commercially from the BASF Corporation under the trademark Pluronic®. Such block copolymers may be generally described as polyoxyethylene/polyoxypropylene condensation polymers terminated in primary hydroxyl groups.

The amount of surfactant component, if any, present varies over a wide range depending on a number of factors, for example, the specific surfactant or surfactants being used, the other components in the composition and the like. Often the amount of surfactant is in the range of about 0.005% or about 0.01% to about 0.1% or about 0.5% or about 1.0% or about 2.5% (w/v).

Useful buffering agents include, but not limited to, acetate buffers, citrate buffers, phosphate buffers and borate buffers. Acids and bases may be used to adjust the pH of the present compositions as needed.

Useful wetting agents include, but are not limited to, polyvinyl alcohol, polyoxamers, polyvinyl pyrrolidone, hydroxypropyl methyl cellulose and mixtures thereof.

Useful sequestering agents include, but are not limited to, disodium ethylene diamine tetraacetate, alkali metal hexametaphosphate, citric acid, sodium citrate and mixtures thereof.

Useful tonicity adjustors include, but are not limited to, sodium chloride, potassium chloride, mannitol, dextrose, glycerin, propylene glycol and mixtures thereof.

Useful viscosity builders include, but are not limited to, hydroxyethyl cellulose, hydroxypropyl methylcellulose, carboxymethyl cellulose, polyvinyl pyrrolidone, polyvinyl alcohol and mixtures thereof.

Useful antioxidants include, but are not limited to, sodium metabisulfite, sodium thiosulfate, N-acetylcysteine, butylated hydroxyanisole, butylated hydroxytoluene and mixtures thereof.

The present compositions may also be used in the care of a contact lens, for example, to make wearing the lens safe and comfortable. The present compositions, formulated appropriately, may be used in conventional contact lens care regimens by using the present compositions in place of prior conventional compositions. In many instances, these contact lens care regimens involve contacting the lens with the present composition in an amount, and at conditions, effective to obtain the beneficial or desired contact lens care result.

Gene Therapy

In a specific embodiment, nucleic acids comprising sequences encoding the mucocidin peptide are administered to treat, inhibit or prevent a disease or disorder associated with microorganism infections or aberrant expression and/or activity of the peptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5): 155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a mucocidin polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijistra et al., Nature 342:435-438 (1989).

Delivery of the nucleic acids into a patient may be either direct, in which case the patient is directly exposed to the nucleic acid or nucleic acid- carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijistra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Subtracted cDNA Library

Human submandibular gland was obtained from a 35 year old man, who received radical neck dissection surgery due to squamous cell carcinoma involving left mandible. The use of human tissue samples for this study was approved by the ethics committee of Kangnung National University in accordance with the guideline provided by Korean Ministry of Health and Welfare. The submandibular gland was normal in postoperative pathological examination. Total RNA was extracted from the fresh tissue by guanidinium thiocyanate-phenol-chloroform method, and mRNA was prepared by use of Oligotex (Qiagen, Valencia, Calif., USA). A cDNA library of human submandibular gland was constructed in the Uni-ZAP XR vector (Stratagene, La Jolla, Calif., USA) by use of mRNA from human submandibular gland and ZAP-cDNA® Gigapack® III Gold Cloning Kit (Stratagene). cDNA of salivary gland was subtracted with cDNA of immortalized human keratinocyte cell line, RHEK cell line (NIH, Bethesda, Md., USA). The phage cDNA library was converted into a pBluescript phagemid cDNA library by in vivo excision with the ExAssist/SOLR system (Stratagene). The pBluescript phagemid cDNA library was plated on LB plates with ampicillin, IPTG, and X-gal (Sigma, St. Louis, Mo., USA), and white colonies were selected for sequencing[35].

Example 2

Sequencing and Homology Search

Selected clones were cultured overnight in 6 mL ampicillin-LB broth and plasmid DNA prepared by plasmid extraction kit (Bioneer, Korea). Both DNA strands of each clone were sequenced by the dideoxynucleotide chain termination method[36] using the ALF-express auto sequencer (Amersham Pharmacia Biotech, Sunnyvale, Calif., USA) and ALF-express autocycle sequencing kit (Amersham Phamacia Biotech). Homology search for each sequence was performed on the Blast search program of NCBI and antimicrobial peptide database (APD).

Example 3

RT-PCR

A pair of sense and antisense primers, ATG CAC GAC TTC TGG GTA CTG (SEQ ID NO:11) (15-35) and ACA MT GAT TGT CTC CTG GTG (180-160) (SEQ ID NO:12), which sequences is not redundant in GenBank search was targeted for the open reading frame of C77-91 (mucocidin) gene. Oligonucleotide primers were synthesized using a DNA synthesizer (ABI 394, Applied Biosystems). A template cDNA was produced using oligo-dT primed reverse transcriptase (Stratagene) reaction of the RNA preparation from human submandibular gland. Genomic DNA was also extracted from the human submandibular gland using the genomic DNA extraction kit (Bioneer). PCR was simultaneously performed using the primers specific for the open reading frame of mucocidin gene and template DNAs of human submandibular gland cDNA, human genomic DNA, and C77-91 plasmid DNA. The polymerase chain reaction using Taq DNA polymerase (Bioneer) was set at 30 sec at 94° C., 30 sec at 55° C., and 30 sec at 72° C. in sequence for a cycle. The PCR products were analyzed by gel-electrophoresis in 1% Agarose and visualized under UV illuminator following ethidium bromide (1 μg/mL) staining.

Example 4

RNA Probe for in situ Hybridization

The RNA probe for the novel gene was generated from the plasmid vector [pBluescript II SK (−)]. C77-91 clone was linearized by BamHI and XhoI enzyme treatment for the production of antisense and sense probes, respectively. Digoxigenin-UTP-labeled single strand antisense and sense RNA probe were prepared by T7 RNA polymerase and T3 RNA polymerase, respectively, using a RNA labeling kit (Boehringer Mannheim, Indianapolis, Ind.).

Example 5

RNA in situ Hybridization on Human Submandibular Gland

The biopsy specimens taken from human submandibular gland were immediately fixed with 4% paraformaldehyde in PBS, embedded in paraffin and 5 μm sections were prepared by using RNase protection method. After deparaffinization, the sections were treated with proteinase K (10 μg/mL) for 15 minutes at room temperature, and endogenous alkaline phosphatase was inactivated using 0.2 N HCl. Hybridization was performed at 50° C. for 16 hours in a humidified chamber in the 10 mM Tris-HCl pH 7.6 buffer containing 50% formamide, 200 μg/mL tRNA, 1× Denhardt's solution, 10% dextran sulfate, 0.6 M NaCl, 0.25% SDS, and 1 mM EDTA. Slides were washed with 2×SSC solution containing 50% formamide at 55° C. for 30 min, and then rinsed with TNE buffer containing 10 mM Tris-HCl, pH 8.0, 0.5 M NaCl, and 1 mM EDTA at 37° C. for 10 min. Nonhybridized transcripts were digested with 20 μg/mL RNase A (Sigma, St. Louis, Mo.) in TNE buffer at 37° C. for 30 min. The slides were washed with TNE buffer at 37° C. for 10 min, then once with 2×SSC at 50° C. for 20 min, and twice with 0.2×SSC at 50° C. for 20 min.

Detection of in situ hybridization was carried out using the Genius Detection system (Boehringer Mannheim). Specifically, transcripts were detected with an anti-digoxigenin antibody conjugated to alkaline phosphatase in the solution 1 (0.1 M maleic acid, 0.15 M NaCl, adjusted to pH 7.5). The slides were washed several times with solution 3 (0.1 M Tris-HCl, pH 9.5 buffer containing 0.1 M NaCl and 50 mM $MgCl_2$) and then immersed in a color-development solution (0.3 mg/mL Nitro Blue Tetrazolium and 0.15 mg/mL of 5-bromo-4-chloro-3-indolyl phosphate in 0.1 M $NaHCO_3$) (Boehringer Mannheim). Color development was stopped by placing the slide into solution 4 (10 mM Tris-HCl buffer pH 8.0 containing 1 mM EDTA)[37].

Example 6

Northern Blot Analysis

Northern blot analysis of mucocidin mRNA was carried out by similar methods described previously[38]. A human submandibular gland tissue was obtained during the neck dissection procedure for oral cancer surgery. The submandibular gland was normal through postoperative pathological examination. Total RNA was extracted from the submandibular glands using an acid-guanidinium-phenol-chloroform method[38]. Single-step method of RNA isolation by acid guanidinium thiocyanate-phenol-chloroform extraction was used[39]. The RNA pellets were stored at −80° C. until used. Twenty micrograms of total RNA were separated on a 1% Agarose, 1M formaldehyde gel and transferred to Nylon membranes (Magna NT, Micron Separation Inc.). A mucocidin cDNA (C77-91 clone) was labeled with biotinylated-dCTP using a random primer labeling kit (BD Biosciences, Palo Alto, Calif.), hybridized at 45° C., and visualized by chemiluminescent detection (BD Biosciences, Palo Alto, Calif.). To normalize the amount of RNA present in the blots, β-actin probe (corresponding to nt 541-1201 of GenBank NM_001101) was also used in the same method.

Example 7 mRNA Array Analysis

Mucocidin cDNA was hybrididized on the mRNA array membrane (BD Biosciences, Palo Alto, Calif.), containing the mRNA extracts from esophagus, stomach, duodenum, jejunum, ileum, ileocecum, appendix, ascending colon, transverse colon, descending colon, rectum, spleen, lung, trachea, bladder, uterus, prostate, pancreas, thyroid gland, salivary gland, mammary gland, and ovary. The mucocidin cDNA was labeled with biotinylated dCTP using Klenow fragment of DNA polymerase I and a mixture of random primers (6-10 nucleotides long), and visualized by chemiluminescent detection (BD Biosciences).

Example 8

Isolation of Human Salivary Mucocidin

Thirty milliliters of parotid saliva from each volunteer was collected into the tube containing 1.0 ml of 0.25 M citrate buffer, pH 4.0 containing 0.02% $NaN_3$. The 10 ml acidified saliva was adsorbed into SP-Sepharose column (2.4×6 ml) equilibrated with 0.025 M citrate buffer pH 4.0, the column was washed with 3 fold column volume each of the equilibrating buffer and the 0.05 M tris-acetate buffer pH 6.0 containing 1 mM EDTA. The mucocidin was eluted with the 0.05 M tris-acetate buffer, pH 6.0 containing 0.15 M NaCl. The eluted mucocidin containing fractions assayed by immunodot blot analysis were pooled and concentrated in Speed-vac centrifuge evaporation apparatus. Pooled mucocidin fractions were applied to Superose 12 column equilibrated with 0.02 M tris-acetate buffer pH 6.0. Two of the mucocidin peaks were detected first at 8 kDa molecular weight marker and next far beyond the column volume.

Reapplication of first eluted peak fraction on the same column resulted in the similar two peak height ratio distribution suggesting that two peak distribution was likely due to mucocidin affinity equilibrium with gel-matrix rather than the specific mucocidin molecule interacting to gel-matrix. Analysis of the second peak mucocidin showed a single band in SDS PAGE analysis with PAS Stain, Western Blot, and Protein stain (no other bands were detected). Both salivary mucocidin fractions showed bacteriocidal activity similar to mucocidin peptides.

Example 9

Antibody Production

Full length mucocidin synthesized (AnyGen, Korea) was conjugated with Keyhole Limpet Hemocyanin (Calbiochem, San Diego, Calif., U.S.A.) for the enhancement of antibody production. Polyclonal antibody against the synthetic peptide was produced in New Zealand white rabbits by multi-site dermal immunization of the emulsified Freund's complete adjuvant (Pierce, Rockford, Ill., U.S.A.). Following booster treatment 3 times at two week intervals, the antiserum was collected. Monospecific antibody was affinity purified by using the antigen affinity gel column using AminoLink® Coupling gel (Pierce)[39] and stored in −75° C. Monoclonal antibody was custom prepared by Coram Bioscience, Korea.

Example 10

Immunohistochemistry

The biopsy specimens taken from normal intact submandibular gland, oral mucosa, lip, skin epithelium, prostate gland, and tissue sections from oral squamous cell carcinoma were fixed with 10% buffered formalin solution, embedded in paraffin and 5 μm sections were prepared. Tissue sections were deparaffinized, hydrated, and endogenous peroxidases were inactivated using 3% hydrogen peroxide for 10 min. The sections were treated to block any non-specific protein interaction with immunoglobulin using normal goat serum (DAKO), and three-layer immuno-labeling was performed with those prepared monospecific antibodies. The sections were incubated with a biotinylated secondary anti-rabbit IgG antibody followed by streptavidin-peroxidase. Immunolocalization was visualized by diaminobenzidine (DAB, Sigma)[40]. As a negative control, the monospecific antibody was pre-absorbed with the synthetic peptide of each gene, and then was applied in the same immunostaining procedure described above.

Example 11

Western-blot Analysis

Parotid saliva from healthy volunteers were collected into tubes containing a cocktail of protease inhibitors, i.e., phenylmethylsulfonyl fluoride (1 mM), aprotonin (0.3 mM), and leupeptin (1 mM) (Roche) using a disc cup apparatus[41], the mixed saliva was collected into the tube containing the same protease inhibitors following thorough rinsing of mouth, and any exfoliated cells present is removed by centrifugation. The collected saliva was quickly heat denatured by boiling in water bath for 10 min with 2% SDS buffer containing reducing agent and 6M urea. Fresh tissue specimens taken from human adult submandibular glands were homogenized in the extraction buffer (0.05 M Tris, pH 8.5, 1 mM EDTA) containing the same protease inhibitors, using a Polytron (Tekmar, Cincinnati, Ohio, U.S.A.) on ice and cell debris were removed by centrifugation. The soluble protein extracts (approximately 30 μg of each) were denatured as stated above.

Western blot analysis was carried out as described previously[42] using Novex Tricine SDS buffer system (Invitrogen). Proteins from the SDS PAGE gel was electro-transferred on to a Nylon filter sheet. Or, soluble proteins to be immuno-blotted was adsorbed on to a Nylon filter sheet (PVDF, Millipore, Bedford, Mass., U.S.A.) in the slot filtering apparatus (Bio-Rad Lab, Hercules, Calif., U.S.A.) and was immediately blocked in TBST buffer (50 mM Tris-HCl, pH 8.0 buffer containing 0.15 M NaCl, 0.1% and Tween-20) with the addition of 5% dry nonfat-milk for 30 min at room temperature. After washing with TBST, the filter was incubated to a fresh solution of TBST containing a 1:1000 dilution of the antibody at room temperature overnight. The filter was then washed with TBST and incubated with a 1:2000 dilution of biotinylated goat anti-rabbit IgG for 1 hour followed by streptavidin-peroxidase. After washing several times with TBST, the filter was immersed in the DAB color-development solution (Sigma)[43].

Example 12

Peptide Preparation

Various sizes of mucocidin peptides were all custom-synthesized (AnyGen, Kwangju; Korea and PeptRon, Daejeon, Korea). HPLC and MS assays were performed by the company to analyze the purity of the peptides. In general, between 85 and 95%, the purity was taken into consideration in the preparation of the stock solution of each peptide for antimicrobial assays.

Example 13

Isolation of Mucocidin from Human Parotid Saliva

Saliva from parotid glands was collected into 0.05 M citrate buffer, pH 4.0.

Example 14

Antimicrobial Assay of Mucocidin

A) Vector Expression of Mucocidin on *E. coli* Growth.

Five hundred *E. coli* (SOLR strain, Stratagene) cells containing C77-91 clone (mucocidin cDNA inserted into pBluescript SK(−) plasmid) and a control *E. coli* containing pBluescript SK(−) plasmid were cultured with 20 ml of Ampicillin-LB broth (one liter solution containing 10 g tryptone, 5 g yeast extract, 5 g NaCl, 1 mL 1 N NaOH, and 100 µg/mL ampicillin) in shaking incubator (37° C., 150 rpm) for 3-5 days. Cell growth was monitored by absorbance at 600 nm. Induction of the vector expression was carried out by addition of 20 µL isopropyl-b-D-thiogalactopyranoside (IPTG 1 mM, Sigma) into the LB broth.

B) Antimicrobial Activity Examination of Synthetic Mucocidin Peptide.

*E. coli* (ATCC 20922) ($5 \times 10^5$ cells) in 100 µL of 10 mM Phosphate Buffer, pH 7.0 containing mucocidin peptide concentration of 5, 10, 15, 20, or 50 µM was incubated for an hour. Then, it was diluted 200 fold with the same buffer and 300 µL aliquots (approx. 750 cells) were plated on 150 mm LB plate and grown overnight at 37° C. The grown colonies were counted. The cell viability was estimated by the percent of colony forming units. *Staphylococcus aureus* (ATCC 25923) and methicillin resistant *Staphylococcus aureus* (MRSA) (ATCC 700698) were incubated with mucocidin concentration up to 5 µM. *Candida albicans* (ATCC 10231) were incubated with mucocidin concentration levels up to 50 µM[44].

C) Scanning Electron Micrography of Microbes Treated with Mucocidin

Scanning Electron Micrographs were taken of *E. coli, Staphylococcus aureus* and *Candida albicans* incubated with 10, 40, 100 µM mucocidin, respectively for 10, 20 and 30 min, and they were immediately fixed with glutaraldehyde, dried on Millipore membrane, and coated with gold. Abnormal morphologies of each microbe were noted for loss and shrinkage of original cell shapes as time lapsed. All photographs were taken at the same magnification.

Example 15

Mucocidin as a Possible Substrate for Transglutaminase

Mucocidin as a transglutaminase substrate was carried out by a slightly modified method of previously described[27] using guinea pig liver transglutaminase (Sigma, St. Luois, Mo.). Transglutaminase assay was carried out by adding 10 µl of enzyme (10 µg) into 90 µL of reaction mixture containing 0.05 M tris acetate buffer, pH 8.0,1 mM EDTA, 5 mM dithiothreitol, 10 mM $CaCl_2$, 0.2% lubrol, and 10 µM of monodansylcadaverine (MDC)(Sigma) and mucocidin (50 µM). Ten µL aliquot of the reaction mixture was removed at 20, 40, 60 and 120 min and added into 500 µL volume of 1 mM EDTA solution to halt the enzyme reaction. Unreacted MDC in solution was extracted with n-hexane. The reacted mucocidin in aqueous solution was blotted on a cellulose nitrate membrane in a slot filtering apparatus (Bio Rad Lab) and washed once with 0.5 mL of water. Relative fluorescence was indicated as a measure of MDC incorporated mucocidin. The aliquots taken from each sample was analyzed on SDS-PAGE. MDC incorporated peptide bands were found to co-migrate with 5 kDa mucocidin peptide band (Data not shown).

Example 16

Isolation and Characterization of Mucocidin Gene

Of those non-redundant clones identified from human submandibular gland gene library, 13 clones were found to show characteristic positive expressions in the salivary epithelium by RNA in situ hybridization. One of the clones, C77-91 was selected and characterized fully for its complete DNA sequences, deduced amino acid sequence, the recombinant protein expression, and protein functional analysis.

The results showed that C77-91 clone was found to be a novel gene whose translated 46 amino acid peptide possesses bactericidal effect on *E. coli* and was registered as 'salvic' earlier at NCBI GenBank accession number, AY177672[23] and redesignated as "mucocidin" considering its dominant expression in mucous epithelia and its possible role in the mucosal cavity (FIG. 1A). Northern blot analysis of mucocidin gene carried out with the freshly dissected human submandibular gland RNA showed a significant expression level of mucocidin mRNA in reference to β-actin mRNA that was used as the control (FIG. 1B). Characterization of mucocidin cDNA showed that it is composed of 527 bp encoding an open reading frame (+15−+155) and expresses 46 amino acids peptide (pI=9.45, 5,252 Da) containing 8 serine, 8 valine, 6 leucine and one cysteine residue in the central region. The hydrophobic residues are clustered in the N-terminal domain, while hydrophilic residues including 4 basic amino acids are gathered in the C-terminal domain together with the consensus sequences of asparagine glycosylation site, protein kinase C phosphorylation site, and a glutamine, transglutaminase-catalyzed crosslinking site (FIG. 1A). PCRs targeted to the open reading frame of mucocidin gene when performed using the template DNAs, i.e., cDNA of human submandibular gland, human genomic DNA, and the plasmid DNA of C77-91 clone, all showed the same expected size band, about 165 bp (FIG. 1C). The nucleotide size of mucocidin gene closely resembles the size of mucocidin cDNA characterized from gene library.

Example 17

Antimicrobial Activity of Mucocidin

Initial attempts to express mucocidin in E. coli resulted in the arrest of cell growth. During the examination of bacterial growth in LB broth, the E. coli transfected with pBluscript vector containing mucocidin gene showed a significant growth retardation during 3 days of incubation; displaying no cell growth after one day, the cell density of 0.4 absorbance at 600 nm ($A_{600}$) at two days, and 0.7 at three days (FIG. 2A).

The control group cells containing vector alone showed rapid growth reaching a plateau with cell density of 2.3 ($A_{600}$) in two days (FIG. 2A). Furthermore, when the E. coli culture was supplemented with a promoter, IPTG (1 mM), the E. coli transfected with mucocidin gene showed severe growth arrest where its cell growth was not detectable until $5^{th}$ day, while the control E. coli overgrew within 2 days (FIG. 2A). These results of bactericidal activity of mucocidin expressed in E. coli were directly confirmed by using the purified synthetic peptide (AnyGen, Korea) of the coding sequence of mucocidin gene. The primary growth of E. coli containing the mucocidin peptide was inhibited in a dose-dependent manner (FIG. 2B). Cells treated with mucocidin in concentrations of 5, 10, 15 and 20 μM showed decrease of colony forming unit (CFU) percentages of 20, 40, 50, and 60, respectively. The mucocidin effect on the primary growth of Staphylococcus aureus (ATCC 255923) was ten fold more sensitive than those on E. coli (FIG. 2B). Comparison of relative mucocidin sensitivity toward microbes; E. coli (ATCC25922), Staphylococcus aureus (ATCC 255923), methicillin-resistant Staphylococcus aureus (ATCC 700698) and Candida albicans (ATCC 10231), showed minimal bactericidal concentration (MBC)[24] of 40±7.3, 3±0.5, 50±10.9 and 80±13.5 μM, respectively. The methicillin-resistant Staphylococcus aureus (ATCC 700698) that tested to be insensitive to kanamycin and ampicillin, was found to be very sensitive to low concentrations of mucocidin. To explore a possible mechanism of mucocidin elicited bactericidal activity, the progress of morphological alteration of microbes upon the treatment of mucocidin was determined by scanning electron Microscopy. E. coli, Staphylococcus aureus and Candida albicans (FIG. 2C) incubated with 10, 40, 100 μM mucocidin, respectively for various time periods, were immediately fixed, dried, and coated with gold. The control was incubated with equivalent amount of PBS solution.

The results in (FIG. 2C) showed time-lapse images of cells at 0, 10, 20, and 30 min. The changes in cellular morphology and shrinkage became evident even at post 30 min mucocidin treatment. Post 90 min, the cells were in a state of shrunken debris (data not shown). These results indicate that induction of cell membrane leakage is one mechanism of antimicrobial activity.

USP Antimicrobial Test carried out with five organisms, E. coli (ATCC #8739) S. aureus (ATCC #6538), P. aeruginosa (ATCC #9027), Aspergellous niger (ATCC #16404), and Candida albicans (ATCC #10231) by Microtest Laboratory, (Agawam, Mass.) showed that three log dilution of the 23 mer mucocidin synthetic peptide resulted in almost no growth of the organisms. The mucocidin (Microtest Laboratories Test sample #05-03383) met the requirement of the USP Validation of Microbial Recovery.

Example 18

Characterization of Human Salivary Mucocidin

In an effort to isolate and characterize physiological mucocidin, freshly collected human parotid saliva, found to contain greater levels of mucocidin tested by immunoblot analysis, was utilized. Following the initial separation of mucocidin from other salivary proteins through cationic ion exchanger, exclusion chromatography of mucocidin enriched fraction on the Superose 12 (Amersham-G.E.) gel column provided affinity-retarded sieve elution to allow isolation of pure native mucocidin. The isolated mucocidin retained antimicrobial activity against E. coli (data not shown). Initial characterization showed native mucocidin was post-translationally modified via glycosylation as indicated by periodate staining. The isoelectric focusing gel analysis showed a diffuse band focused at pKa value 6.0, a value less than the estimated pKa 9.45 based on the peptide sequence. (FIG. 4D). Analysis of mucocidin on SDS Polyacrylamide gel electrophoresis (PAGE) showed diffuse band in the 50 kDa molecular weight markers identifiable with Western blot and PAS stain (periodate stain) and quite resistant to Coomassie Blue stain (data not shown). On the other hand, gel filtration analysis on Superose 12 column showed apparent molecular size of 8 kD. Thus, there appeared to be anomalous migration on SDS PAGE.

Example 19

Activity Relationship with Peptide Domains

Earlier studies of numerous antimicrobial peptides showed core domains of coded sequence associated with antimicrobial activity mostly in the domain consisting of basic amino acid residues[25]. Bactericidal activity of various deletion peptides of mucocidin (PeptRon, Korea) was compared with the activity of Magainin II (23 mer) peptide (Table 1). Table 1 shows that the native mucocidin peptide possesses good bactericidal activity although the deletion of the amino terminal hydrophobic residues from 1 to $30^{th}$ residue caused some gain of bactericidal activity but this might be due to a problematic solubility of lengthy hydrophobic peptide domain of native peptide in the aqueous buffer in vitro. Also first 15 residue peptide likely functions as propeptide and native peptide will likely have 31 residues. Twenty three mer peptide (24~46 residue) showed no antigenic activity but 35 mer (12~46) synthetic peptide and isolated native salivary mucocidin showed antigenic activity. The Amino terminal peptide ($1^{st}$-$23^{rd}$) peptide showed no activity.

However, when the $31^{st}$ arginine residue was deleted, the bactericidal activity was decreased more than three fold suggesting that basic residues are the key motifs that control the activity. Regardless of the length (17-23 mer), peptides containing four basic amino acids ($31^{st}$-$45^{th}$) all showed similar minimal bactericidal concentration (MBC) comparable with the reference Magainin II (23 mer) peptide. Thus, amino acid residues 31st to 45th containing basic core residues are likely to be an essential domain for cell membrane binding.

Example 20

Expression Pattern of Mucocidin Gene

To gain insight into the broader physiological role of mucocidin, expression of mucocidin gene in various tissues and organs associated with mucous epithelium was examined.

Mucocidin full length cDNA (527 bp) was hybridized on the mRNA array membrane (BD Biosciences, Palo Alto, Calif.), containing the normalized loadings of poly A+RNA from different human tissues; esophagus, stomach, duodenum, jejunum, ileum, ileocecum, appendix, ascending colon, transverse colon, descending colon, rectum, spleen, lung, trachea, urinary bladder, uterus, prostate, pancreas, thyroid gland, salivary gland, mammary gland, and ovary. The mucocidin cDNA was labeled with biotinylated dCTP using Klenlow fragment of DNA polymerase I and a mixture of random primers (6-10 nucleotides long), and visualized by chemiluminescent detection (BD Biosciences, Palo Alto, Calif.). Results shown in (FIG. 5A) indicate that all of the gastrointestinal mucosal epithelial cells show positive mucocidin mRNA expression and especially, colonic epithelial cells show relatively higher expression. In addition, other glandular organs such as prostate, lung, trachea, urinary bladder, uterus, prostate, pancreas, thyroid gland, salivary gland, mammary gland and so on, show positive expression. Spleen and ovary, which reacted negatively can serve as control. Interestingly, prostate gland showed strong positive expression and appeared to be related to finding high levels of mucocidin in the seminal fluid (FIG. 5C). Presence of mucocidin mRNA in the lactating mammary gland is also of great interest for the possible secretion into milk. Examination of cellular mucocidin expression in human submandibular gland by in situ method showed intense expression in the ductal cells of the gland and also minor amounts in some serous acinar cells (FIG. 5B). The sense mRNA and nonsense random nucleotides were used as negative controls. The expression of mucocidin mRNA was more intense in the striated ducts and intralobular excretory ducts, especially localized at the luminal cytoplasm of the ductal cells. No reaction was detected in negative control. For a detailed examination of cellular expression of mucocidin gene in the exocrine gland, submandibular gland was selected for RNA in situ hybridization analysis (FIG. 3B). mucocidin expression was strongly positive in the ductal cells of human submandibular gland and occasionally positive in the acinar cells. In the ductal cells, mucocidin was localized at the juxtanuclear Golgi apparatus area and gradually scattered into the excretory granules in the luminal cytoplasm likely as secretory granules.

To affirm peptide expression, immunohistological staining was carried out on a few selected mucosal and glandular tissues (FIG. 3C). Positive mucocidin antibody reactive sites are indicated by arrows. In the oral mucosa, the buccal epithelium containing differentiated keratinocytes appeared to be the prominent cellular layer stained intensely. Mucocidin was distributed in the superficial layer in a linear fashion. Colonic epithelium showed relatively higher expression among the gastrointestinal epithelia and all focalized at the top exposed segment of villi. Prostate gland showed the highest expression of all glands examined where immune reaction was positive in the tubular epithelium and a lot of secretory granules were detectable at high magnification.

In other exocrine glands, i.e., mammary, lacrimal, sebaceous, sweat gland and pancreas, strong mucocidin expression was detected in the ductal epithelium and also in light expression in acinar cells resembling those of salivary and prostate gland. In lactating mammary gland, there was evidence of mucocidin in milk droplets in the mammary ducts suggesting mucocidin is active component in human milk, while human resting breast showed very little expression in comparison with lactating mammary gland.

A significant level of mucocidin was identified in human tears (data not shown). Mucocidin expressions in the sebaceous and sweat gland indicate that it is secreted on to skin for epidermal protection as evidenced by strong mucocidin immune response seen in the stratum corneum of human skin. Mucosal lining of nasal cavity showed strong mucocidin expression in the olfactory mucosa ciliated epithelia. Stomach epithelium showed focalized distribution on the outer differentiated epithelia again likely suggesting expression and strong binding of mucocidin. Uterus epithelia showed moderate expression as well. These results suggest that mucocidin is actively secreted into body fluid where it is necessary.

Example 21

Covalent Association of Mucocidin to Mucosal Epithelial Cells

These immunological staining of the mucosal epithelium indicate that mucocidin is expressed in the outer layers of epithelium and the secreted peptide remains bound to the epithelial surface. In an effort to probe into the mode of secreted mucocidin association with epithelial cell membrane, the exfoliated epithelial cells collected in the whole mixed saliva were treated in the chaotropic reagent containing 8 M urea, 1% SDS, 2 mM EDTA and 20 mM mercaptoethanol at 100° C. for 2 hours at a time repeatedly until no protein was eluted into soluble phase. The remaining insoluble protein envelopes representing the crosslinked cornified epithelial cell envelopes[26] were paraffin embedded, sectioned and immunostained with the antibody to mucocidin. The results in (FIG. 4A) indicate that collapsed envelope proteins are strongly stained with mucocidin antibody on either the entire surface (FIG. 4Aa) or portion of the surface (FIG. 4Ab), suggesting that mucocidin is indeed covalently attached to epithelial cell envelop proteins. The negative control without mucocidin antibody is shown in (FIG. 4Ac). Based on these results, the most likely candidate for a crosslink site in the mucocidin sequence appears to be the single 37$^{th}$ glutamine residue that is capable of crosslinking to $NH_2$-group of lysine residue catalyzed by transglutaminase (TGase)[27,28]. To test whether mucocidin is a substrate for TGase, the well characterized guinea pig liver TGase (Sigma, St. Louise, Mo.) (also known tissue TGase, TGase 2) was added into the reaction mixtures of amine substrate, monodansylcadaverine (MDC) and mucocidin peptide. The time-dependent uptake of MDC into mucocidin (FIG. 4C) was detected only in the presence of $Ca^{++}$ but not in its absence (FIG. 4C). These results indicate that mucocidin is indeed capable of crosslinking to keratinocyte membrane by salivary or mucosal TGases[28]. Other known salivary proteins (mucosal ligands), such as proline rich protein, cystatin, and histatin are also known to be crosslinked to epithelial cell membranes[12,29-31]. These results provide the evidence for covalent coupling of mucocidin to cell surface of mucosal epithelium to establish stable functional protective barrier.

Example 22

Mucocidin in Mucosal and Glandular Secretions

Since mucocidin appears to be secreted into mucosal fluid and is associated with the epithelia, what proportion of it remains in the fluid? To investigate the state of secreted mucocidin, mucosal fluids from human parotid gland, and seminal fluids were analyzed by Western blot following SDS-PAGE. Submandibular gland extracts which may represent mucocidin stored in cells showed a dominant "50 kDa band" (FIG. 4B lane 3). Seminal fluid and parotid saliva also showed a similar "50 kDa band" (FIG. 4B lane 4) but negligible levels were detected in the mixed saliva (FIG. 4B lane 5). As discussed above, anomalous SDS PAGE migration yielded misrepresentation of molecular weight (MW) as "50 kDa" but MW estimation of 8 kDa by molecular sieve on Superose 12 gel column closely resembles native mucocidin molecular weight. These findings indicate that the secreted mucocidin may also remain in mucosal fluid initially and then eventually is associated with the epithelia.

Example 23

Ophthalmic Composition with Mucocidin

The following composition is prepared by blending together the ingredients.

| Ingredient | % w/v |
| --- | --- |
| mucocidin | 0.0001 |
| Castor Oil | 1.25 |
| Glycerine | 2.2 |
| Polysorbate 80 | 1.0 |
| Cyclosporin A | 0.1 |
| Carbomer (stabilizer) | 0.05 |
| Purified Water | Q.S. to 100% |

This composition is formulated as and is effective as a composition for the treatment of dry eye.

Example 24

Ophthalmic Composition with Mucocidin

The following composition is prepared by blending together the ingredients.

| Ingredient | % w/v |
| --- | --- |
| mucocidin | 0.0001 |
| Hydroxyethyl cellulose | 0.65 |
| Sodium chloride | 0.67 |
| Boric acid | 0.39 |
| Sodium borate decahydrate | 0.20 |
| Edetate disodium | 0.127 |
| Purified Water | Q.S. to 100% |

This composition is formulated as and is effective as a preserved soft contact lens cleaning composition.

REFERENCES

1. Otte, J. M., Kiehne, K. & Herzig, K. H. Antimicrobial peptides in innate immunity of the human intestine. *J Gastroenterol* 38, 717-26 (2003).

2. Ganz, T. Antimicrobial proteins and peptides in host defense. *Semin Respir Infect* 16, 4-10 (2001).

3. Boman, H. G. Innate immunity and the normal microflora. *Immunol Rev* 173, 5-16 (2000).

4. Zasloff, M. Antimicrobial peptides in health and disease. *N Engl J Med* 347, 1199-200 (2002).

5. Zasloff, M. Antimicrobial peptides of multicellular organisms. *Nature* 415, 389-95 (2002).

6. Sansonetti, PJ. War and peace at mucosal surfaces. *Nat Rev Immunol* 4, 953-64 (2004).

7. Imler, J. L. & Hoffmann, J. A. Toll receptors in innate immunity. *Trends Cell Biol* 11, 304-11 (2001).

8. Hertz, C. J. et al. Activation of Toll-like receptor 2 on human tracheobronchial epithelial cells induces the antimicrobial peptide human β defensin-2. *J Immunol* 171, 6820-6 (2003).

9. Backhed, F. & Hornef, M. Toll-like receptor 4-mediated signaling by epithelial surfaces: necessity or threat? *Microbes Infect* 5, 951 -9 (2003).

10. Dale, B. A. & Krisanaprakornkit, S. Defensin antimicrobial peptides in the oral cavity. *J Oral Pathol Med* 30, 321-7 (2001).

11. Dale, B. A. et al. Localized antimicrobial peptide expression in human gingiva. *J Periodontal Res* 36, 285-94 (2001).

12. Oppenheim, J. J., Biragyn, A., Kwak, L. W. & Yang, D. Roles of antimicrobial peptides such as defensins in innate and adaptive immunity. *Ann Rheum Dis* 62 Suppl 2, ii 17-21 (2003).

13. Boman, H. G. Peptide antibiotics and their role in innate immunity. *Annu Rev Immunol* 13, 61-92 (1995).

14. Zasloff, M. Magainins, a class of antimicrobial peptides from Xenopus skin: isolation, characterization of two active forms, and partial cDNA sequence of a precursor. *Proc Natl Acad Sci USA* 84, 5449-53 (1987).

15. Ganz, T. & Lehrer, R. I. Antimicrobial peptides of vertebrates. *Curr Opin Immunol* 10, 41-4 (1998).

16. Gennaro, R. & Zanetti, M. Structural features and biological activities of the cathelicidin-derived antimicrobial peptides. *Biopolymers* 55, 31-49 (2000).

17. Frohm, M. et al. The expression of the gene coding for the antibacterial peptide LL-37 is induced in human keratinocytes during inflammatory disorders. *J Biol Chem* 272:, 15258-15263 (1997).

18. Ganz, T. et al. Defensins. Natural peptide antibiotics of human neutrophils. *J Clin Invest* 76, 1427-35 (1985).

19. Ganz, T. Defensins and host defense. *Science* 286, 420-421 (1999).

20. Agerberth, B. et al. FALL-39, a putative human peptide antibiotic, is cysteine-free and expressed in bone marrow and testis. *Proc Natl Acad Sci USA* 92, 195-9 (1995).

21. Zanetti, M., Gennaro, R., Scocchi, M. & Skerlavaj, B. Structure and biology of cathelicidins. *Adv Exp Med Biol* 479, 203-18 (2000).

22. Schittek, B. et al. Dermcidin: a novel human antibiotic peptide secreted by sweat glands. *Nat Immunol* 2, 1133-7 (2001).

23. Kim, Y. S. & Lee, S. K. Homo sapiens salivary gland antimicrobial salvic (SALV) mRNA. (GenBank (NCBI), 2003).

24. Sambri, V. et al. Comparative in vitro activity of five cathelicidin-derived synthetic peptides against Leptospira, Borrelia and Treponema pallidum. *J Antimicrob Chemother* 50, 895-902 (2002).

25. Boman, H. G. Antibacterial peptides: basic facts and emerging concepts. *J Intern Med* 254, 197-215 (2003).

26. Candi, E. et al. Biochemical, structural, and transglutaminase substrate properties of human loricrin, the major epidermal cornified cell envelope protein. *J Biol Chem* 270, 26382-90 (1995).

27. Folk, J. E. & Chung, S. I. Transglutaminases. *Methods Enzymol* 113, 358-75 (1985).

28. Kim, H. C. et al. Protransglutaminase E from guinea pig skin. Isolation and partial characterization. *J Biol Chem* 265, 21971-8 (1990).

29. Bradway, S. D., Bergey, E. J., Jones, P. C. & Levine, M. J. Oral mucosal pellicle. Adsorption and transpeptidation of salivary components to buccal epithelial cells. *Biochem J* 261, 887-96 (1989).

30. Bradway, S. D. et al. Formation of salivary-mucosal pellicle: the role of transglutaminase. *Biochem J* 284 (Pt 2), 557-64 (1992).

31. Yao, Y., Lamkin, M. S. & Oppenheim, F. G. Pellicle precursor proteins: acidic proline-rich proteins, statherin, and histatins, and their crosslinking reaction by oral transglutaminase. *J Dent Res* 78, 1696-703 (1999).

32. Zalewska, A., Zwierz, K., Zolkowski, K. & Gindzienski, A. Structure and biosynthesis of human salivary mucins. *Acta Biochim Pol* 47, 1067-79. (2000).

33. Lee, C. H. et al. Small proline-rich protein 1 is the major component of the cell envelope of normal human oral keratinocytes. *FEBS Lett* 477, 268-72 (2000).

34. Ganz, T. Defensins: antimicrobial peptides of innate immunity. *Nat Rev Immunol* 3, 710-20 (2003).

35. Sambrook, J. & Russell, D. W. *Molecular coning: a laboratory manual,* 11.1-11.123 (Cold Spring Harbor Laboratory Press, New York, 2001).

36. Sanger, F., Nicklen, S. & Coulson, A. R. DNA sequencing with chain—terminating inhibitors. *Proc Natl Acad Sci* 74, 5463-7 (1977).

37. Lee, S. K. et al. Improved technique of digoxigenin labeled RNA in situ hybridization. *Kor J Pathol* 35, 98-110. (2001).

38. Lee, S. K. et al. Molecular cloning, chromosomal mapping, and characteristic expression in tooth organ of rat and mouse Krox-25. *Genomics* 83, 243-53 (2004).

39. Ausubed, F. M. et al. Current protocols in molecular biology 15.0.1-15.8.7 (John Wiley & Sons, New York, 1998).

40. Beesley, J. E. *Immunocytochemistry: a practical approach,* (Oxford, N.Y., 1993).

41. Shaeffer, M. E., Rhodes, M., Prince, S., Michalek, S. M. & McGhee, J. R. A plastic device for the collection of human parotid saliva. *J Dent Res* 56, 728-33 (1977).

42. Lee, S. K. et al. Elafin expression in human fetal and adult submandibular glands. *Histochem Cell Biol* 117, 423-30 (2002).

43. Harlow, E. & Lane, D. Using antibodies: a laboratory manual. 267-310 (Cold Spring Harbor Laboratory Press, New York, 1999).

44. Situ, H., Wei, G., Smith, C. J., Mashhoon, S. & BoBbek, L. A. Human salivary MUC7 mucin peptides: effect of size, charge and cystein residues on antifungal activity. *Biochem. J.* 375, 175-182 (2003).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

TABLE 1

Amino acid sequence and MBC of mucocidin peptides

| Peptide | amino acid sequence* | Net charge** | S. aureus (MBC, µM) |
| --- | --- | --- | --- |
| 46-mer | $M^1$HDFWVLWVLLEYIYNSACSVLSATSSVSSRVLNRSLQVKVVKITN$^{46}$ (SEQ ID NO:2) | +2 | >70.0 |
| 35-mer | $E^{12}$YIYNSACSVLSATSSVSSRVLNRSLQVKVVKITN$^{46}$ (SEQ ID NO:3) | +3 | >50.0 |
| 23-mer-N | $M^1$HDFWVLWVLLEYIYNSACSVLS$^{23}$ (SEQ ID NO:4) | -2 | no activity |
| 23-mer-C | $A^{24}$TSSVSSRVLNRSLQVKVVKITN$^{46}$ (SEQ ID NO:5) | +4 | >10.0 |
| 21-mer | SSVSSRVLNRSLQVKVVKITN (SEQ ID NO:6) | +4 | >3.5 |
| 19-mer | VSSRVLNRSLQVKVVKITN (SEQ ID NO:7) | +4 | >3.5 |
| 17-mer | SRVLNRSLQVKVVKITN (SEQ ID NO:8) | +4 | >5.0 |
| 15-mer | VLNRSLQVKVVKITN (SEQ ID NO:9) | +3 | >20.0 |
| 16-mer | SRVLNRSLQVKVVKIT (SEQ ID NO:10) | +4 | >5.0 |
| Magainin II (23-mer) | $G^1$IGKFLHSAKKFGKAFVGEIMNS$^{23}$ (SEQ ID NO:13) | +3 | >3.0 |

*Numbers in mucocidin sequence indicate residue numbers of the native mucocidin
**Net charge of peptides at pH 7.0
MBC: minimal bactericidal concentration

What is claimed is:

1. A therapeutic antimicrobial composition comprising a glycosylated mucocidin antimicrobial peptide, or fragment thereof, having antimicrobial activity.

2. The composition according to claim 1, wherein the fragment consists of 12 amino acid residues.

3. The composition according to claim 1, wherein the fragment consists of 20 amino acid residues.

4. The composition according to claim 1, wherein the fragment consists of 22 amino acid residues.

5. The composition according to claim 1, wherein the fragment consists of 24 amino acid residues.

6. The composition according to claim 1, wherein the fragment consists of 26 amino acid residues.

7. The composition according to claim 1, wherein said fragment has at least four basic amino acids.

8. The composition of claim 1, wherein said peptide or fragment is glycosylated at an asparagine residue.

9. The composition of claim 1, wherein said fragment is represented by any one of SEQ ID NOs:5-10.

10. An ophthalmic composition comprising a carrier component, and a mucocidin antimicrobial peptide, or a fragment thereof with antimicrobial activity, and mixtures thereof, wherein said composition is an oil-containing emulsion or an oil-containing suspension.

11. The composition of claim 10, wherein said mucocidin antimicrobial peptide, or fragment thereof, is present in an effective amount less than about 10 milligrams per milliliter.

12. The composition of claim 11, which further comprises an effective amount of a tonicity component to provide said composition with a desired osmolality.

13. The composition of claim 10, wherein said composition comprises a mucocidin antimicrobial peptide fragment of 12, 20, 22, 24, or 26 amino acid residues.

14. The composition of claim 10, wherein said composition comprises a fragment with the sequence of one of SEQ ID NOs: 5-10.

15. A therapeutic antimicrobial composition comprising a mucocidin antimicrobial peptide variant with antimicrobial activity and a sequence of at least 90% identity to
  i) SEQ ID NO:2;
  ii) positions 16-46 of SEQ ID NO:2; or
  iii) a fragment of either i) or ii);
  wherein said variant does not have a sequence represented by SEQ ID NO:2.

16. The composition of claim 15, wherein said variant is represented by a sequence of at least 96% identity to SEQ ID NO:2.

17. The composition of claim 15, wherein said variant is represented by a sequence of at least 98% identity to SEQ ID NO:2.

18. The composition of claim 15, wherein said variant is glycosylated.

19. A method of inhibiting microbial growth, said method comprising contacting a subject with the composition according to claim 1 to inhibit growth of a microbe.

20. The method according to claim 19, wherein the composition comprises a glycosylated mucocidin peptide fragment comprising at least four basic residues.

21. The method according to claim 19, wherein the microbe is bacteria, virus or fungus.

22. The method according to claim 19, wherein the composition comprises a glycosylated mucocidin peptide fragment with the sequence of one of SEQ ID NOs: 5-10.

* * * * *

SEQUENCE LISTING

<160> NUMBER OF SEQ ID NOS: 13

<210> SEQ ID NO 1
<211> LENGTH: 527
<212> TYPE: DNA
<213> ORGANISM: Homo sapiens

<400> SEQUENCE: 1
gttttattta gcgtatgcac gacttctggg tactgtgggt tcttttggaa tatatatata      60
attccgcgtg tagtgtactg tcagctacgt caagtgtgag cagccgggtg ttaaacagaa     120
gtctccaggt gaaggtggtt aaaatcacca actgattctc accaggagac aatcatttgt     180
tgtattacac gttttcttaa attctatgtt caaattttct aattagttat tatccaaagg     240
ttacttttgg tgaatgtgag gaatcaactg acacaaatag acaaagtcgt aaaataaaaa     300
cctaaatctg cactttgaat gttttggaca aaatattcta aaatctaaaa gttgatcagt     360
gcaagagaaa cgatgtaatg tctgtgatgt ctcaccttca gattgtggct tcagtaccgt     420
gattatgcaa tattagttat gtatgtatgt atattagtta ttatgtaata ttagtgtgat     480
gagcaaaaga aaagaatta aaaaataaaa tgggtgaaaa aaaaaaa                    527

<210> SEQ ID NO 2
<211> LENGTH: 46
<212> TYPE: PRT
<213> ORGANISM: Homo sapiens

<400> SEQUENCE: 2

Met His Asp Phe Trp Val Leu Trp Val Leu Leu Glu Tyr Ile Tyr Asn
1               5                   10                  15

Ser Ala Cys Ser Val Leu Ser Ala Thr Ser Ser Val Ser Ser Arg Val
            20                  25                  30

Leu Asn Arg Ser Leu Gln Val Lys Val Val Lys Ile Thr Asn
        35                  40                  45

<210> SEQ ID NO 3
<211> LENGTH: 35
<212> TYPE: PRT
<213> ORGANISM: Homo sapiens

<400> SEQUENCE: 3

Glu Tyr Ile Tyr Asn Ser Ala Cys Ser Val Leu Ser Ala Thr Ser Ser
1               5                   10                  15

Val Ser Ser Arg Val Leu Asn Arg Ser Leu Gln Val Lys Val Lys
            20                  25                  30

Ile Thr Asn
        35

<210> SEQ ID NO 4
<211> LENGTH: 23
<212> TYPE: PRT
<213> ORGANISM: Homo sapiens

<400> SEQUENCE: 4

Met His Asp Phe Trp Val Leu Trp Val Leu Leu Glu Tyr Ile Tyr Asn
1               5                   10                  15

Ser Ala Cys Ser Val Leu Ser
            20

```
<210> SEQ ID NO 5
<211> LENGTH: 23
<212> TYPE: PRT
<213> ORGANISM: Homo sapiens

<400> SEQUENCE: 5

Ala Thr Ser Ser Val Ser Ser Arg Val Leu Asn Arg Ser Leu Gln Val
1               5                   10                  15

Lys Val Val Lys Ile Thr Asn
            20

<210> SEQ ID NO 6
<211> LENGTH: 21
<212> TYPE: PRT
<213> ORGANISM: Homo sapiens

<400> SEQUENCE: 6

Ser Ser Val Ser Ser Arg Val Leu Asn Arg Ser Leu Gln Val Lys Val
1               5                   10                  15

Val Lys Ile Thr Asn
            20

<210> SEQ ID NO 7
<211> LENGTH: 19
<212> TYPE: PRT
<213> ORGANISM: Homo sapiens

<400> SEQUENCE: 7

Val Ser Ser Arg Val Leu Asn Arg Ser Leu Gln Val Lys Val Val Lys
1               5                   10                  15

Ile Thr Asn

<210> SEQ ID NO 8
<211> LENGTH: 17
<212> TYPE: PRT
<213> ORGANISM: Homo sapiens

<400> SEQUENCE: 8

Ser Arg Val Leu Asn Arg Ser Leu Gln Val Lys Val Val Lys Ile Thr
1               5                   10                  15

Asn

<210> SEQ ID NO 9
<211> LENGTH: 15
<212> TYPE: PRT
<213> ORGANISM: Homo sapiens

<400> SEQUENCE: 9

Val Leu Asn Arg Ser Leu Gln Val Lys Val Val Lys Ile Thr Asn
1               5                   10                  15

<210> SEQ ID NO 10
<211> LENGTH: 16
<212> TYPE: PRT
<213> ORGANISM: Homo sapiens

<400> SEQUENCE: 10

Ser Arg Val Leu Asn Arg Ser Leu Gln Val Lys Val Val Lys Ile Thr
1               5                   10                  15

<210> SEQ ID NO 11
<211> LENGTH: 21
<212> TYPE: DNA
```

```
<213> ORGANISM: Artificial Sequence
<220> FEATURE:
<223> OTHER INFORMATION: Primer

<400> SEQUENCE: 11
atgcacgact tctgggtact g                                              21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
acaaatgatt gtctcctggt g                                              21

<210> SEQ ID NO 13
<211> LENGTH: 23
<212> TYPE: PRT
<213> ORGANISM: Xenopus sp.

<400> SEQUENCE: 13

Gly Ile Gly Lys Phe Leu His Ser Ala Lys Lys Phe Gly Lys Ala Phe
1               5                   10                  15

Val Gly Glu Ile Met Asn Ser
            20
```